(12) United States Patent
Omary et al.

(10) Patent No.: US 9,796,743 B2
(45) Date of Patent: Oct. 24, 2017

(54) BIDENTATE HETEROLEPTIC SQUARE PLANAR COMPLEXES OF (PYRIDYL)AZOLATES

(71) Applicant: University of North Texas, Denton, TX (US)

(72) Inventors: Mohammad A. Omary, Denton, TX (US); Iain W. H. Oswald, Plano, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 235 days.

(21) Appl. No.: 14/536,092

(22) Filed: Nov. 7, 2014

(65) Prior Publication Data

US 2015/0155504 A1 Jun. 4, 2015

Related U.S. Application Data

(60) Provisional application No. 61/911,969, filed on Dec. 4, 2013.

(51) Int. Cl.
*C07F 15/00* (2006.01)
*C09K 11/06* (2006.01)
*H01L 27/092* (2006.01)

(52) U.S. Cl.
CPC .......... *C07F 15/0093* (2013.01); *C09K 11/06* (2013.01); *C09K 2211/185* (2013.01); *H01L 27/092* (2013.01)

(58) Field of Classification Search
CPC .............. C09K 11/06; C09K 2211/185; H01L 51/0087; H01L 51/5206; H01L 51/5016; H01L 51/5221; H01L 27/092; C07F 15/0093
See application file for complete search history.

(56) References Cited

U.S. PATENT DOCUMENTS 7,002,013 B1 * 2/2006 Chi ...................... C07D 403/14
502/167
8,580,397 B2 11/2013 Omary

FOREIGN PATENT DOCUMENTS

WO 2010/016990 2/2010
WO 2014/189073 11/2014

OTHER PUBLICATIONS

Hsieh et al, Platinum(II) complexes with spatially encumbered chelates; syntheses, structure and photophysics, Inorganica Chimica Acta, vol. 362, Issue 13, pp. 4734-4739, Oct. 15, 2009.*
European Patent Office; International Search Report and Written Opinion; PCT Application No. PCT/US2014/068270; Feb. 19, 2015.
European Patent Office; International Preliminary Report on Patentability; PCT Application No. PCT/US2014/068270; mailed by the International Bureau of WIPO on Jun. 16, 2016.
D'Andrade, B. W.; Forrest, S. R. "White Organic Light-Emitting Devices for Solid-State Lighting", Adv. Mater. 2004, 16, 1585.
D'Andrade, B. W.; Adamovich, V.; Thompson, M. E.; Forrest, S. "White Light Emission Using Triplet Excimers in Electrophosphorescent Organic Light-Emitting Devices" Adv. Matt. 2002, 14, 1032.
Bhansali, U.; Polikarpov, E.; Swensen, J. S.; Chen, W.-H.; Jia, H.; Gaspar, D. J.; Gnade, B. E.; Padmaperuma, A. B.; Omary, M. A., Appl. Phys. Lett. 2009, 95, 233304.
Misra, A.; Kumar, P. ; Kamalasanan, M. N. ; Chandra, S. "White organic LEDs and their recent advancements", Semicond. Sci. Technol. 2006, 21, R35-R47.
Myznikov, L.V.; Roh, J.; Artamonova, T.V.; Hrabalek, A.; Koldobskii, G.I. Russ. J. Org. Chem. 2007, 43, 765-767.
Newman, C. R.; Frisbie, C. D.; da Silva Filho, D. A.; Bredas, J.-L.; Ewbank, P. C.; Mann, K. R. "Introduction to Organic Thin Film Transistors and Design of n-Channel Organic Semiconductors" Chem. Mater. 2004, 16, 4436.
Sloop, J.C.; Bumgardner, C.L.; Washington, G.; Loehle, W.D.; Sankar, S.S.; Lewis, A.B. J. Fluor. Chem. 2006, 127, 780-786.
Thiel, W.R.; Eppinger, J. Chem. Eur. J. 1997, 3, 696-705.
Wang, Q.; Oswald, I. W. H.; Perez, M. R.; Huiping, J; Gnade, B. E.; Omary, M. A. Adv. Funct. Mater. 2013, 23, 5420-5428.

* cited by examiner

*Primary Examiner* — Alexander Kollias
(74) *Attorney, Agent, or Firm* — Jackson Walker LLP

(57) ABSTRACT

Bidentate heteroleptic square planar complexes of (pyridyl) azolates possess optical and electrical properties that render them useful for a wide variety of optical and electrical devices and applications. In particular, the complexes are useful for obtaining white or monochromatic organic light-emitting diodes ("OLEDs"), including doping-free OLEDs. Preferred forms also demonstrate semiconducting behavior and may be useful in a variety of other applications. Within the general complexes of (pyridyl)azolates, the metal and the ligands may be varied to impart different optoelectronic properties.

23 Claims, 22 Drawing Sheets

BIDENTATE HETEROLEPTIC SQUARE PLANAR COMPLEXES OF (PYRIDYL)AZOLATES

This application claims priority to U.S. Provisional Patent Application Ser. No. 61/911,969, entitled "BIDENTATE HETEROLEPTIC SQUARE PLANAR COMPLEXES OF (PYRIDYL)AZOLATES," filed Dec. 4, 2013, the entire content of which is incorporated by reference.

The present invention used in part funds from the National Science Foundation Grant No. CHE-0911690. The United States Government has certain rights in the invention.

BACKGROUND

This invention pertains to bidentate square planar heteroleptic complexes of (pyridyl)azolate ligands, and particularly to their use in organic light emitting diodes ("OLEDs"), semi-conducting materials, and other applications.

Luminescent organic or metal-organic molecular materials have a range of applications. These include organic light emitting diodes ("OLEDs") that exhibit white or monochrome electroluminescence. Such devices may be utilized in solid-state lighting ("SSL"), which accounts for 22% of total electrical power consumption in the U.S., and also for video display in electronic devices such as TV, camcorders, monitors, cell phones, etc. In particular, utilization of phosphorescent metal-organic complexes in OLEDs has allowed higher device performance than that allowed by fluorescent organic materials because the phosphorescent metal-organic complexes allow radiative recombination of both triplet and singlet excitons (with an upper limit of 100% efficiency compared to 25% for fluorescent organic materials).

Traditional OLED fabrication methods require doping in order to achieve high efficiencies. This is problematic for multiple reasons: Precise control over the doping concentration is difficult and can lead to inhomogeneity in thin films thus affecting performance and color rendering. Second, incomplete host-guest charge transfer and charge leakage results in decreased efficiency that become especially burdensome at higher voltages. It is therefore desirable to eliminate the need for doping in an OLED device while maintaining high performance.

Another area of intense interest is in organic thin film transistors "OTFTs". These devices, along with other organic electronics, rely on p-type and/or n-type semiconducting materials to function properly. Although p-type semiconducting organic materials have been realized with high hole mobilities, n-type semiconductors which conduct electrons have not been able to maintain the same performance.

SUMMARY

The present disclosure relates generally to a class of metal-organic complexes that possess optical and electrical properties which make them useful for a variety of optical and electronic devices and applications. The materials are heteroleptic square planar complexes of (pyridyl)azolate ligands with a variety of substituents and metal ions such as Pt(II), Pd(II), and Ni(II). This disclosure also pertains to organic light emitting diodes ("OLEDs"). This disclosure also pertains to organic thin film transistors ("OTFTs"), and more particularly to n-type OTFTs. This disclosure also pertains to semiconducting metal-organic materials.

The heteroleptic square planar complexes of (pyridyl)azolate ligands preferably have the structure shown below:

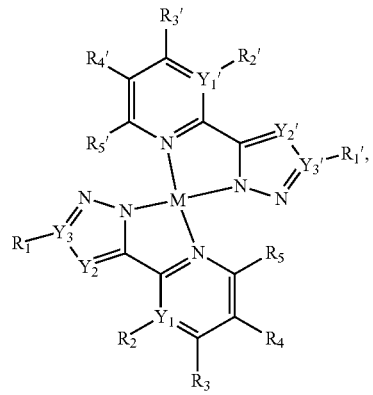

wherein all variable positions shown this structure ($R_1$, $R_2$, $R_3$, $R_4$, $R_5$, $R_1'$, $R_2'$, $R_3'$, $R_4'$, $R_5'$, $Y_1$, $Y_2$, $Y_3$, $Y_1'$, $Y_2'$, $Y_3'$) are chosen such that the two bidentate ligands do not equal one another. In other words, they are heteroleptic. The following are possible functional groups: $Y_1$ and $Y_2$ may be C—H or N; $Y_3$ may be C—H, C—R, or N, but may be C—R only when $R_2$ and/or $R_2'$ do not equal H; $R_1$ and $R_1'$ may be H, $CF_3$, $C_3F_7$, $C_6F_5$, $C_6H_5$, $CH_3$, or $C_5H_4N$; $R_2$ and $R_2'$ may be H, $CH_3$, $CF_3$, $C_3F_7$, $C_2H_5$, $C_3H_7$, $C_6H_5$, $C_6F_5$, or $C_5H_4N$; $R_3$ and $R_3'$ may be H, $CH_3$, $CF_3$, $C_3F_7$, $C_2H_5$, $C_3H_7$, $C_6H_5$, $C_6F_5$, $C_{10}H_7$ (naphthalene), $C_{13}H_9$ (fluorene), $C_{14}H_9$ (anthracene), $C_5H_4N$, or N9-linked $C_{12}H_8N$ (carbazole); $R_4$ and $R_4'$ may be H, $CH_3$, $CF_3$, $C_3F_7$, $C_2H_5$, $C_3H_7$, $C_6H_5$, $C_6F_5$, $C_{10}H_7$ (naphthalene), $C_{13}H_9$ (fluorene), $C_{14}H_9$ (anthracene), N9-linked $C_{12}H_8N$ (carbazole), or $C_5H_4N$; $R_5$ and $R_5'$ may be H or F; and M may be Pt, Pd, or Ni.

Use of the bidentate heteroleptic square planar complexes of (pyridyl)azolate ligands allows for highly simplified OLED device structures with different emission chromaticity. OLED devices typically consist of at least five layers: an anode, electron transfer layer (ETL), emissive layer (EML), hole transport layer (HTL), and cathode. Furthermore, the emissive materials typically have to be doped at a very specific concentration within the EML in order to achieve high quantum efficiency and power efficiency. Likewise, the ETL and HTL are often doped with conductivity dopants in order to attain high power efficiency. Each of these layers is burdensome to fabricate and elimination of at least one layer or one material within a doped layer while still maintaining high power or quantum efficiency and total functionality of the device is highly sought after. The present disclosed Pt(II) heteroleptic compounds and OLED devices made from said compounds satisfy both of these needs while offering other substantial benefits, including the opportunity to modify the heteroleptic ligands to provide improved solubility in solvents, thus making these materials suitable for various printing processes, as well as changing emission chromaticity.

The metal-organic complexes in this invention can also be useful as n-type molecular materials for use in thin-film transistors ("TFTs") and diodes (light-emitting or otherwise) and other types of optical or electronic devices that utilize organic semiconductors. The said complexes usually exist in different packing forms in their crystalline thin films or solid powders, including forms in which molecules are arranged as dimers, oligomers, and extended linear chains, each with a different degree of overlap between the stacked units of the complex. All these aggregated forms lead to imparting a greater extent of the n-type semiconducting behavior in a neat or highly-doped thin film than the dissociated form that exists in dilute solutions or thin films that are doped in a host matrix at a low concentration of the complex.

DETAILED DESCRIPTION OF PREFERRED EMBODIMENTS

Figure 1:
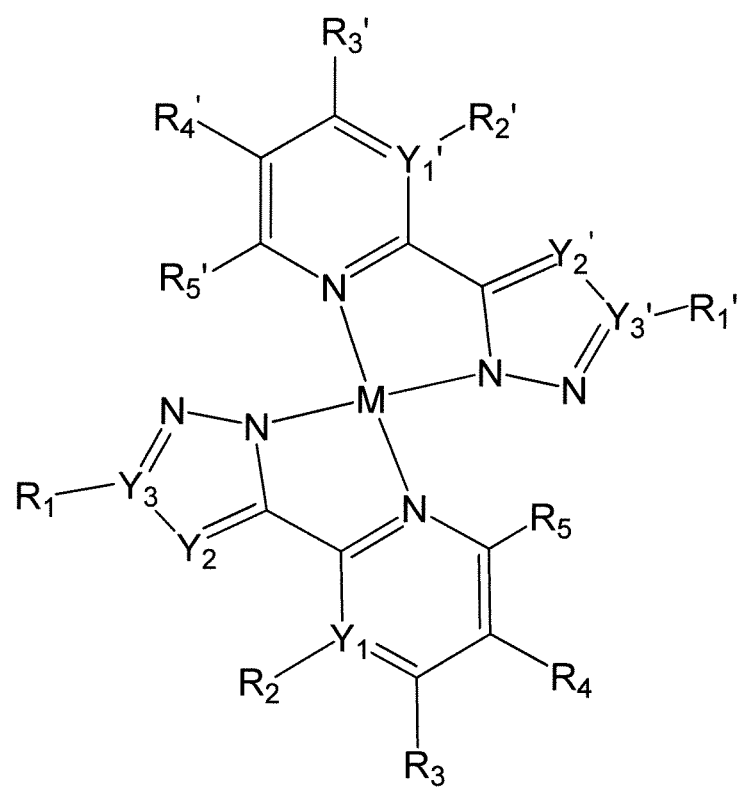
FIG. 1 shows the general structural formula for the heteroleptic square planar complexes of (pyridyl)azolate ligands.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

Generally, the present disclosure relates to bidentate heteroleptic square complexes of (pyridyl)azolates in which two different (pyridyl)azolate ligands are coordinated simultaneously to a metal center. The complexes herein exhibit bright phosphorescence of varying emissive colors, high quantum yields that approach unity in the thin film form, and short radiative lifetimes.

The bidentate heteroleptic square complexes of (pyridyl) azolates preferably have the structure shown in FIG. 1 below:

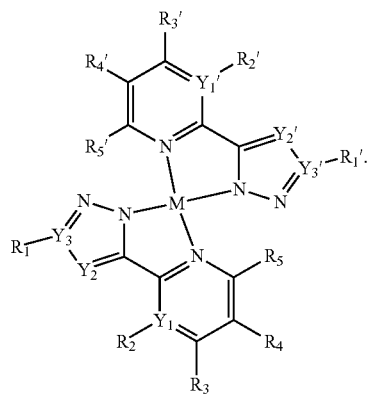

Two different bidentate ligands are shown, complexed to M in the center. In this structure, all variable positions shown ($R_1$, $R_2$, $R_3$, $R_4$, $R_5$, $R_1'$, $R_2'$, $R_3'$, $R_4'$, $R_5'$, $Y_1$, $Y_2$, $Y_3$, $Y_1'$, $Y_2'$, $Y_3'$) are chosen such that the two bidentate ligands do not equal one another. In other words, they are heteroleptic. The following are possible functional groups for inclusion in the two bidentate ligands: $Y_1$ and $Y_2$ may be C—H or N; $Y_3$ may be C—H, C—R, or N, but may be C—R only when $R_2$ and/or $R_2'$ do not equal H; $R_1$ and $R_1'$ may be H, $CF_3$, $C_3F_7$, $C_6F_5$, $C_6H_5$, $CH_3$, or $C_5H_4N$; $R_2$ and $R_2'$ may be H, $CH_3$, $CF_3$, $C_3F_7$, $C_2H_5$, $C_3H_7$, $C_6H_5$, $C_6F_5$, or $C_5H_4N$; $R_3$ and $R_3'$ may be H, $CH_3$, $CF_3$, $C_3F_7$, $C_2H_5$, $C_3H_7$, $C_6H_5$, $C_6F_5$, $C_{10}H_7$ (naphthalene), $C_{13}H_9$ (fluorene), $C_{14}H_9$ (anthracene), $C_5H_4N$, or N9-linked $C_{12}H_8N$ (carbazole); $R_4$ and $R_4'$ may be H, $CH_3$, $CF_3$, $C_3F_7$, $C_2H_5$, $C_3H_7$, $C_6H_5$, $C_6F_5$, $C_{10}H_7$ (naphthalene), $C_{13}H_9$ (fluorene), $C_{14}H_9$ (anthracene), N9-linked $C_{12}H_8N$ (carbazole), or $C_5H_4N$; $R_5$ and $R_5'$ may be H or F; and M may be Pt, Pd, or Ni. It is possible that one or more among $R_1$, $R_2$, $R_3$, $R_4$, $R_5$, $R_1'$, $R_2'$, $R_3'$, $R_4'$, $R_5'$, $Y_1$, $Y_2$, $Y_3$, $Y_1'$, $Y_2'$, and $Y_3'$ is/are identical on the two ligands as long as at least one other $R_1$, $R_2$, $R_3$, $R_4$, $R_5$, $R_1'$, $R_2'$, $R_3'$, $R_4'$, $R_5'$, $Y_1$, $Y_2$, $Y_3$, $Y_1'$, $Y_2'$, or $Y_3'$ is different in the other ligand coordinated to the same metal center.

Phosphorescent materials exhibiting high quantum yields in the neat (doping-free) form are highly desirable due to the unique properties allowing for simplification of OLED device structures. An advantage of the phosphorescent materials of this disclosure compared to previous phosphorescent materials is the ability to achieve high quantum yields in the neat form as opposed to a doped form.

Phosphors exhibiting blue emission have been the most problematic color in the production of OLED devices. There are examples utilizing doping methodologies known in the art to obtain blue emission, but to date there are very few neat blue phosphors. The discovery and incorporation of a neat blue phosphor into a device would be advantageous in order to simplify device design while increasing efficiency. Disclosed herein is a blue emitting neat form of one of the species that can be used in OLED devices to generate blue phosphorescence.

The phosphorescent lifetime of the excited state of the emissive material can affect the efficiency of a device. Longer lifetimes result in multiple quenching mechanisms manifesting themselves at higher drive voltages. The current disclosed complexes have lifetimes that are short, typically less than 1 microsecond, reducing quenching processes such as triplet-triplet annihilation and triplet-polaron annihilation as shown for their homoleptic counterparts (see Wang, et al. 2013 and Omary 2013), resulting in the observed high device efficiency, which is required for high-performance OLED devices. The heteroleptic embodiments offer yet additional significant advantages over their homoleptic congeners known in the state-of-the-art OLED materials, as outlined throughout this disclosure.

Thermal evaporation is a commonly used method for fabricating OLED devices. Therefore, it is advantageous to have electrically, chemically and thermally stable phosphors in order to survive the thermal evaporation process. The complexes disclosed have excellent chemical stability in the presence of air showing no signs of decomposition after months of exposure to the atmosphere. They also possess high thermal stability with no significant change in composition less than 300° C.

Soluble phosphorescent materials are highly sought after due to the ability to use them in solution casting thin film fabrication methods, such as spin coating, roll-to-roll processing, or inkjet printing processes used for the fabrication of OLED devices. It is therefore advantageous to have soluble phosphors that can be utilized in these processes. Two example species screened in this disclosure have demonstrated excellent solubility in common solvents such as tetrahydrofuran (THF), acetone, dioxane, as well as mixtures of common organic solvents. This indicates these materials can have varying chemical functionality to increase solubility yet still retain excellent photophysical properties.

In preferred embodiments, the bidentate heteroleptic sequare complexes of (pyridyl)azolates may be [(5-(2-pyridyl)-1,2,3,4-tetrazolato)(3-trifluoromethyl-5-(2-pyridyl)-1,2-pyrazolato)]Platinum(II)("PTD"), [(5-(5-phenyl-2-pyridyl)-1,2,3,4-tetrazolato)(3-trifluoromethyl-5-(2-pyridyl)-1,2-pyrazolato)]Platinum(II) ("PTE"), [(5-(2-pyridyl)-1,2,3,4-tetrazolato)(3-heptafluoropropyl-5-(2-pyridyl)-1,2-pyrazolato)]Platinum(II) ("PTF"), [(5-(5-phenyl-2-pyridyl)-1,2,3,4-tetrazolato)(3-heptafluoropropyl-5-(2-pyridyl)-1,2-pyrazolato)]Platinum(II) ("PTG"), [(5-(6-methyl-2-pyridyl)-1,2,3,4-tetrazolato)(3-trifluoromethyl-5-(2-pyridyl)-1,2-pyrazolato)]Platinum(II) ("PTH"), [(5-(4-fluoro-2-pyridyl)-1,2,3,4-tetrazolato)(3-trifluoromethyl-5-(2-pyridyl)-1,2-pyrazolato)]Platinum(II) ("PTI"), or [(5-(4-fluoro-2-pyridyl)-1,2,3,4-tetrazolato)(3-heptafluoropropyl-5-(2-pyridyl)-1,2-pyrazolato)]Platinum(II) ("PTJ").

The photoluminescence (PL) behavior for this series of preferred embodiments includes monomer emission in solution for soluble species and extended excimeric emission for solids of the pure compounds. All exhibit broad excimeric emission in the solid state indicating aggregation is present. Electrical characteristics of PTD in an electron-only single carrier device show high electron mobilities at low voltages, while showing negligible current in hole-only single carrier devices. These phenomena suggest that these materials could function as both the electron transporting layer (ETL) and emissive layer (EML) in an OLED device. This was confirmed by using PTD operating concomitantly as both the ETL and EML in highly efficient doping-free OLED devices, achieving a maximum power efficiency of 82 lm/W, and an EQE of ~19% with a low threshold voltage of 2.9V, as discussed further in Example 3 below.

The photoluminescent properties of the preferred embodiments are shown in FIGS. 3-11 and discussed further in Example 2 below. These data demonstrate that a wide range of emissive colors from turquoise blue (~505 nm) to orange (~590 nm) can be achieved. The photophysical properties are summarized in Table 1 below, showing the high efficiency of the materials in the powder form and/or thin film form.

TABLE 1

Room temperature photophysical properties of Pt(II) complexes.

| Species | $\lambda_{excitation\ max}$ | $\lambda_{emission\ max}$ | $\Phi$ | $\tau$ (ns) |
|---|---|---|---|---|
| PTD-1 | 430 | 505 | 0.28 | 1400 |
| PTD-2 | 495 | 550 | 0.65 | 1261 |
| PTD-3[a, b] | 480[a], 343[b] | 580[a], 580[b] | 0.78[a], 0.98[b] | 916[a], 468[b] |
| PTE | 485 | 585 | 0.74 | 378 |
| PTF | 373 | 572 | 0.81 | 774 |
| PTG | 475 | 552 | 0.18 | 523 |
| PTH | 485 | 590 | 0.51 | 382 |
| PTI | 485 | 580 | 0.45 | 324 |
| PTJ | 375 | 535 | 0.56 | 340 |

[a]Powder form,
[b]= thin film.

With regard to varying the metal ("M") in the complexes as they are shown in FIG. 1, the use of palladium (Pd) favors the formation of n-type OTFTs. Nickel (Ni) is a good choice for the metal because it is more cost-effective than Pt or Pd for both OLEDs and OTFTs. Changing the ligands (R or R') to H is designed to increase the chances to create better stacking of the complexes so as to render greater conductivity or fine-tune the PL or EL properties. Varying the substituents on the ligands can change the optical, chemical, or electrical properties. Solubility can be increased by using n-alkyl groups or n-fluoroalkyl groups. Increased rigidity and chromophoric character can be imparted by use of phenyl, polyaromatics, carbazole derivatives, or other aromatic species, increasing electronegativity with fluorinated substituents, increase nitrogen content of at least one azolate moiety to three (1,2,4-triazolate), or four (1,2,3,4-tetrazolate) can help tune the emission color.

The bidentate square complexes can be used to obtain white, near-white, and monochrome OLEDs that utilize the electroluminescence of PTD and other material variations disclosed herein. This includes near-white OLEDs based on EL emission of PTD. This also includes white and near-white OLEDs based on a combination of the EL emissions of PTD and another emitter in the same device. Monochrome OLEDs (including blue) can also be obtained using the EL emission of PTD. White and near-white OLEDs and monochrome OLEDs (including blue) can also be obtained using EL emission of bidentate square planar platinum(II) complexes of (pyridyl)azolates, with or without another emitter in the same device. White and near-white OLEDs and monochrome OLEDs (including blue) can also be obtained using EL emission of bidentate square planar nickel(II) complexes of (pyridyl)azolates, with or without another emitter in the same device. Acceptable ranges of concentration of the complexes within the CBP solid matrix can be deter mined intuitively as further described in the examples below. Altering the concentration of the complexes allows a shift in the color scheme.

Since pyridyl(azolate) ligands in general are rather electron poor, the conductivity is unipolar is selective for electrons instead of holes, as discussed further below. The combination of this unipolar property and the extended chain stacking motif render square-planar pyridyl(azolate) complexes ideal for use as n-type semiconductors in organic field-effect transistors (OFETs)—also known as organic thin film transistors (OTFTs), which are the central components of electronic devices. Varying the metal (M) or the substituent ($R_x$ and $Y_x$) allows control of the extent of the n-type conducting behavior and/or facilitates the deposition of the materials into the functional thin film form needed for the devices by either thermal evaporation (sublimation) of solids or casting from solution (spin coating or inkjet printing).

Applications of the bidentate heteroleptic square complexes of (pyridyl)azolates include OTFTs, n-type OTFTs, and CMOS devices including an n-type semiconductor. These devices can be obtained using bidentate heteroleptic square planar palladium(II) complexes of (pyridyl)azolates, bidentate heteroleptic square planar nickel(II) complexes of (pyridyl)azolates, and bidentate heteroleptic square planar platinum(II) complexes of (pyridyl)azolates. Square planar complexes of (pyridyl)azolates can be used to create conducting and semiconducting solids (thin films, single crystals, or pressed pellets).

EXAMPLE 1

Synthesis

All pyridyl(tetrazoles) were synthesized following a modified previously reported procedure (Myznikov, et al. 2007). Pyridyl(pyrazoles) were synthesized following previously reported procedures (Sloop, et al. 2006 and Thiel, et al. 1997).

2-(tetrazol-5-yl)pyridine (ttzpH) was synthesized as follows. Into a 35 mL microwave vessel was placed a stir bar, 15 mL of deionized water, 2-cyanopyridine (5 mmol, 0.52 g), sodium azide (5.5 mmol, 0.36 g) and zinc(II) chloride (5 mmol, 0.68 g). The reaction was stirred under the conditions of microwave radiation and the power was adjusted to maintain 95° C. for two hours. Upon cooling, concentrated hydrochloric acid was added drop wise to the mixture while stirring to adjust the pH to 1. After stirring for one hour, the solid material was filtered, washed with cold water and dried under vacuum. Yield 74%.

4-phenyl-2-(tetrazol-5-yl)pyridine (ttzphpH) was synthesized as follows. Into a 35 mL microwave vessel was placed a stir bar, 15 mL of deionized water, 2-cyano-4-phenylpyridine (5 mmol, 0.90 g), sodium azide (5.5 mmol, 0.36 g) and zinc(II) chloride (5 mmol, 0.68 g). The reaction was stirred under the conditions of microwave radiation and the power was adjusted to maintain 95° C. for six hours. Upon cooling, concentrated hydrochloric acid was added drop wise to the mixture while stirring to adjust the pH to 1. After stirring for one hour, the solid material was filtered, washed with cold water and dried under vacuum. Yield 72%.

3-methyl-2-(tetrazol-5-yl)pyridine (ttzmpH) was synthesized as follows. Into a 35 mL microwave vessel was placed a stir bar, 15 mL of deionized water, 2-cyano-3-methylpyridine (5 mmol, 0.59 g), sodium azide (5.5 mmol, 0.36 g) and zinc(II) chloride (5 mmol, 0.68 g). The reaction was stirred under the conditions of microwave radiation and the power was adjusted to maintain 95° C. for two hours. Upon cooling, concentrated hydrochloric acid was added drop wise to the mixture while stirring to adjust the pH to 1. After stirring for one hour, the solid material was filtered, washed with cold water and dried under vacuum. Yield 70%.

5-fluoro-2-(tetrazol-5-yl)pyridine (ttzpH) was synthesized as follows. Into a 35 mL microwave vessel was placed a stir bar, 15 mL of deionized water, 2-cyanopyridine (5 mmol, 0.52 g), sodium azide (5.5 mmol, 0.36 g) and zinc(II) chloride (5 mmol, 0.68 g). The reaction was stirred under the conditions of microwave radiation and the power was adjusted to maintain 95° C. for two hours. Upon cooling, concentrated hydrochloric acid was added drop wise to the mixture while stirring to adjust the pH to 1. After stirring for one hour, the solid material was filtered, washed with cold water and dried under vacuum. Yield 74%.

2-(3-(trifluoromethyl)pyrazol-5-yl)pyridine (ppf3H) was synthesized as follows. A dry, two-necked round-bottomed flask was equipped with a stir bar and water condenser. Into the flask was placed sodium ethoxide (50 mmol, 3.40 g) and 100 mL of dry THF. Into two separate Schlenk flasks was placed 50 mL of dry THF, and 2-acetylpyridine (50 mmol, 6.06 g, 5.7 mL) and ethyl 2,2,2-trifluoroacetate (50 mmol, 7.10 g, 6.0 mL), respectively. The ketone/THF solution was added to the NaOEt/THF solution with stirring, followed by the ester/THF solution. After refluxing for six hours, the mixture was cooled to room temperature and the solvent was removed under vacuum. Any remaining NaOEt was quenched, and inorganic impurities were dissolved by the addition of 25-30 mL of 1M sulfuric acid followed by extraction with diethyl ether (2 x 50 mL). The organic extract was dried with magnesium sulfate, vacuum filtered and the solvent was removed to leave a thick oil. A 250 mL two-necked flask was equipped with a stir bar and water condenser. Into the flask, this crude product was dissolved in ethanol (100 mL) followed by the drop wise addition of hydrazine (52.5 mmol, 1.68 g, 1.6 mL) or hydrazine monohydrate (52.5 mmol, 2.63 g, 2.6 mL). After refluxing for five hours, the solvent was removed under vacuum to leave a light yellow powder, which was further purified by sublimation. Yield 49%.

2-(3-(perfluoropropyl)pyrazol-5-yl)pyridine (ppf7H) was synthesized as follows. A dry, two-necked round-bottomed flask was equipped with a stir bar and water condenser. Into the flask was placed sodium ethoxide (50 mmol, 3.40 g) and 100 mL of dry THF. Into two separate Schlenk flasks was placed 50 mL of dry THF, and 2-acetylpyridine (50 mmol, 6.06 g, 5.7 mL) and ethyl perfluorobutanoate (50 mmol, 12.10 g, 8.7 mL), respectively. The ketone/THF solution was added to the NaOEt/THF solution with stirring, followed by the ester/THF solution. After refluxing for six hours, the mixture was cooled to room temperature and the solvent was removed under vacuum. Any remaining NaOEt was quenched, and inorganic impurities were dissolved by the addition of 25-30 mL of 1M sulfuric acid followed by extraction with diethyl ether (2 x 50 mL). The organic extract was dried with magnesium sulfate, vacuum filtered and the solvent was removed to leave a thick oil. A 250 mL two-necked flask was equipped with a stir bar and water condenser. Into the flask, this crude product was dissolved in ethanol (100 mL) followed by the drop wise addition of hydrazine (52.5 mmol, 1.68 g, 1.6 mL) or hydrazine monohydrate (52.5 mmol, 2.63 g, 2.6 mL). After refluxing for five hours, the solvent was removed under vacuum to leave a light yellow powder, which was further purified by sublimation. Yield 36%.

Figure 2:
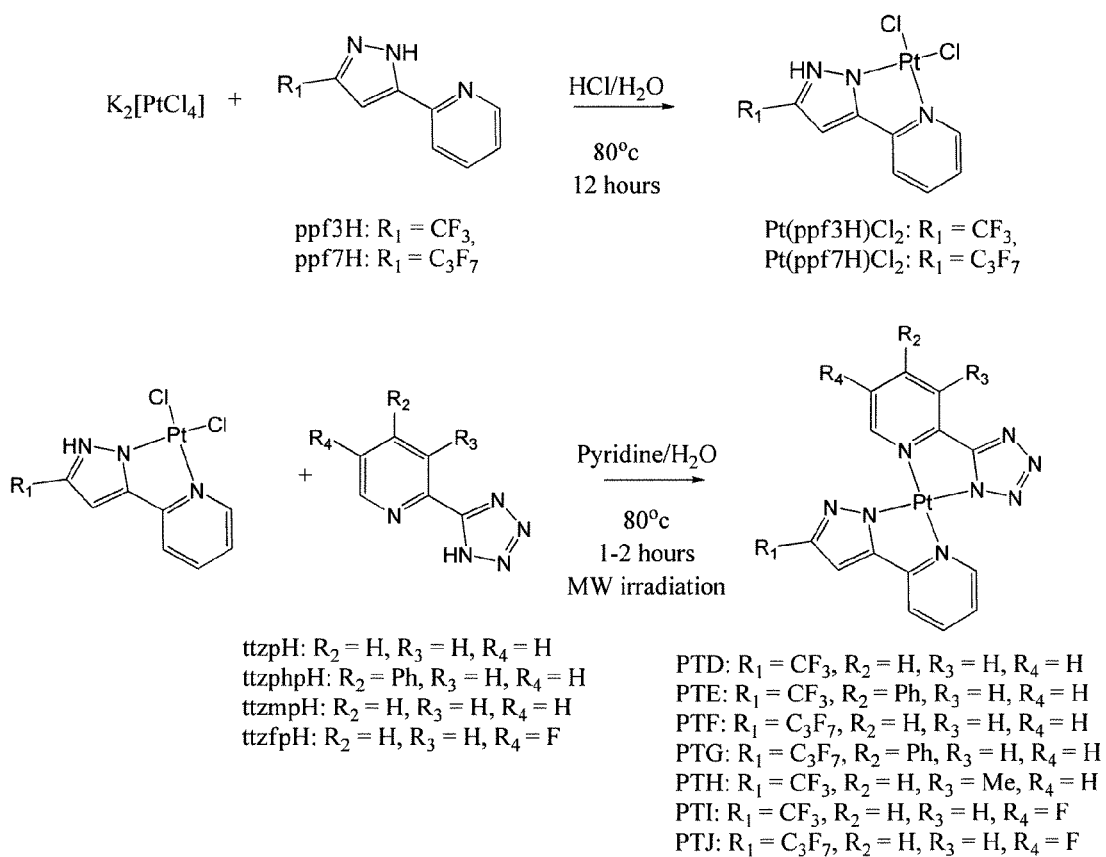
FIG. 2 shows the general scheme for the synthesis of the metal-organic complexes disclosed.

The general synthesis for the bidentate Pt(II) heteroleptic square planar complexes is as follows. To a 50 mL round bottom flask, 1.2 mmol of $K_2[PtCl_4]$ and 1.2 mmol of the respective pyridylpyrazolate ligand were added followed by 30 mL of a 3M solution of HCl in water. This solution was heated and stirred for 12 hours. The solid yellow precipitate was collected, washed with water and acetone, and dried under vacuum. 1.2 mmol of this product and 1.2 mmol the respective pyridyltetrazolate ligand were added to a 100 mL round bottom flask containing 15 mL of pyridine and 5 mL of deionized water. This solution was then stirred at 80° C. for 12-24 hours. The solid precipitate was then collected, washed with water, acetone, and diethyl ether and then dried under vacuum. If needed, the products were then sublimed between 350-400° C. Yields were between 66-80%. This general reaction is shown in FIG. 2.

EXAMPLE 2

Photoluminescence ("PL") Properties of Synthesized Complexes

PTD was found to have three major different emissive forms that have been isolated during its synthesis, depending on the reaction and/or crystallization conditions: PTD-1, which has blue luminescence (505 nm peak maximum), PTD-2, which has green luminescence (550 nm peak maximum), and PTD-3, which has yellow luminescence (580 nm peak maximum). Elemental analysis confirmed all three forms were chemically identical. Therefore, it is most likely their specific packing motifs in the solid state that lead to the varying emissive colors. In the solid state, aggregation is present, thus the emission of these materials is dominated by their intermolecular interactions. The wide range of colors observed for PTD-1, PTD-2, and PTD-3 therefore most likely arise from their varying intermolecular distances.

PTD-3 has bright yellow luminescence with a peak maximum at 580 nm. The emission profile indicates strong aggregation is present, which results in unstructured excimeric emission. The excitation profile is broad with peak maximums at 365 nm and 480 nm with the latter being the major excitation. The relatively unstructured excitation indicates that discrete electronic transitions such as MLCT or $\pi$-$\pi$* are not present but are instead replaced by broad band-like structure. The lack of structure and broad featureless, excitation implies that aggregation is present in the solid form due to excited state mixing. The Stokes shift is relatively small at only 3592 cm$^{-1}$; this small energy gap suggests little energy is lost between the ground state and the emissive excited state, which can translate into smaller energy losses in device performance. PTD-3 in the thin film form, has a near unity quantum yield of 98±4%. The broad, featureless emissions indicate aggregation is present in all materials and suggest that they could function in high efficiency doping-free OLEDs.

Figure 3:
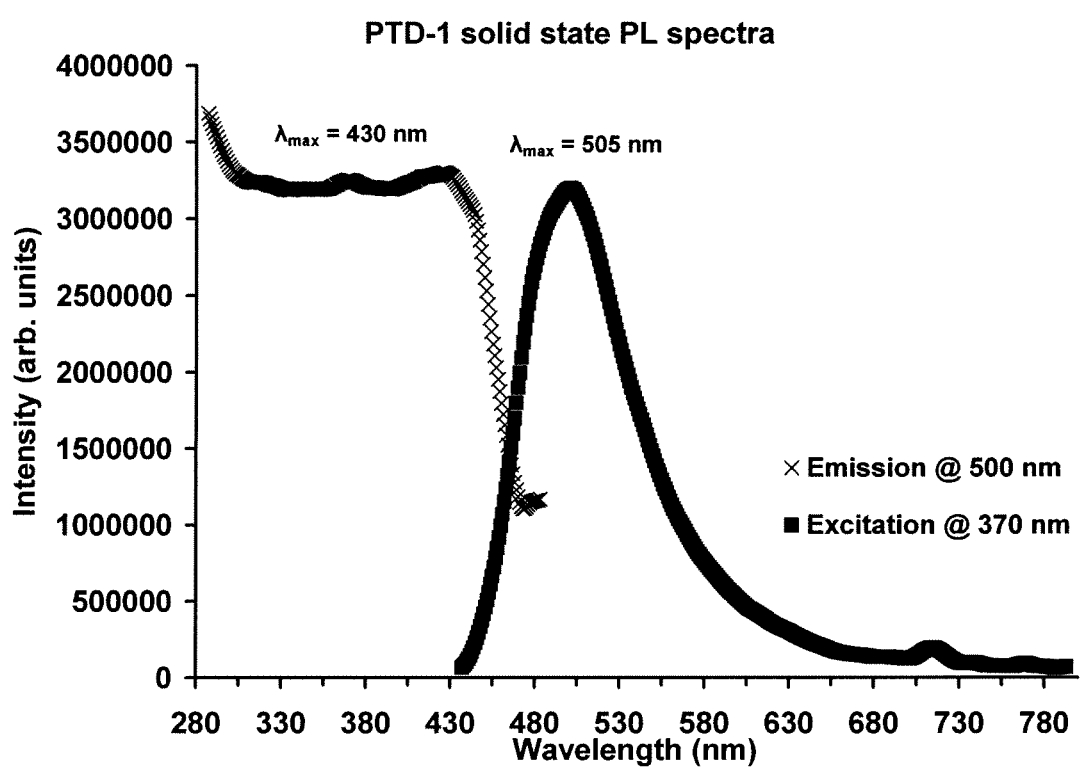
FIG. 3 shows the photoluminescence ("PL") spectra of PTD-1.
Figure 4:
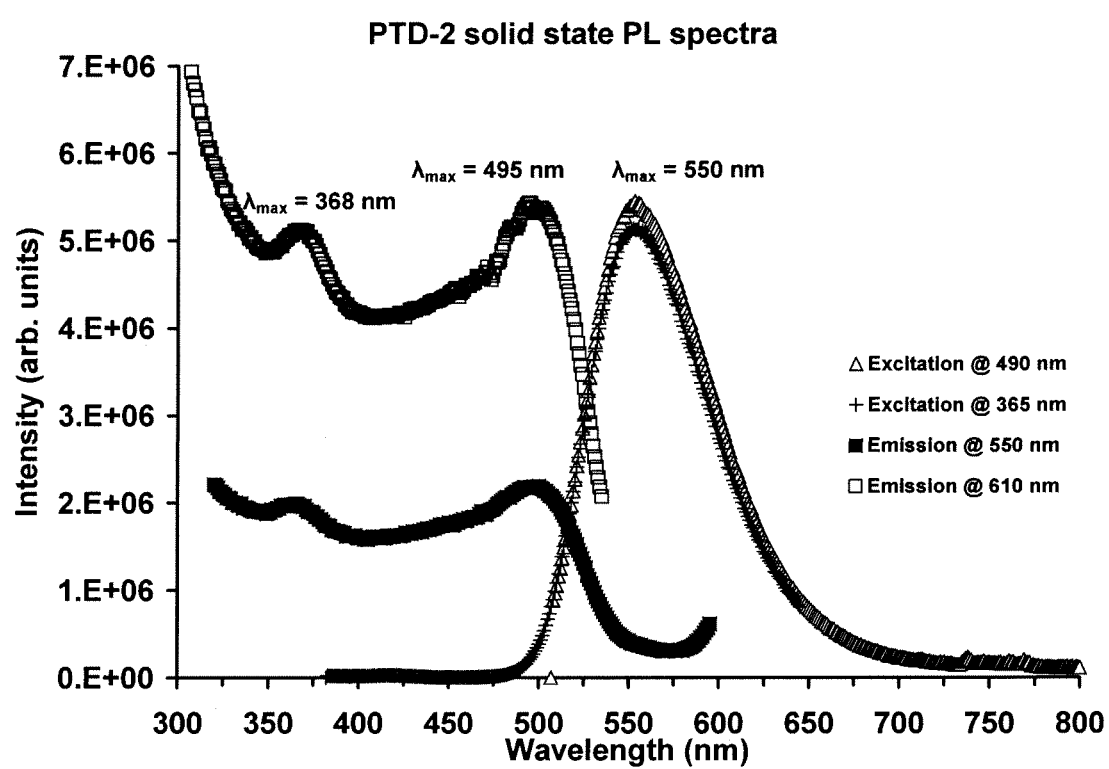
FIG. 4 shows the PL spectra of PTD-2.
Figure 5:
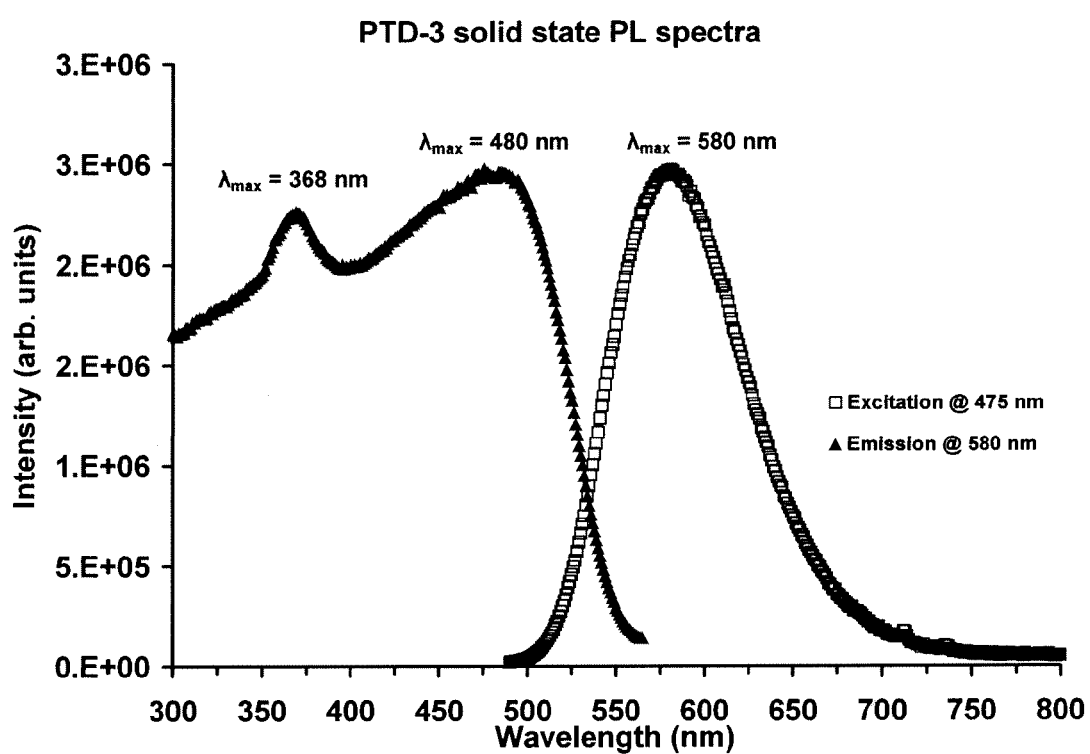
FIG. 5 shows the PL spectra of PTD-3.

PTD-1 has turquoise emission with a peak maximum at 505 nm (seen in FIG. 3). PTD-2 exhibits green-yellow emission with a peak maximum at 550 nm (seen in FIG. 4). It features unstructured emission similar to PTD-3 (seen in FIG. 5) indicating that excimeric emission is the main mode of emission. This indicates that PTD, as an example within this class of materials, could use varying experimental conditions during its synthesis or thin film fabrication to generate different forms of the same material, and thus allow color tuning throughout the visible spectrum.

PTD-1 has a much more blue-shifted emission than PTD-3 or PTD-2. The emission is still unstructured and shows a Gaussian-like profile with a broad band excitation, indicating that there is still strong interaction from neighboring molecules to attain a band structure as opposed to discrete molecular orbitals to represent the electronic structure. There is also a very small Stokes shift of 3353 cm$^{-1}$ and short lifetime of 1400 ns, albeit longer than the PTD-3 form. This would be a rare example of a turquoise blue neat emitter if it could be fabricated into a thin film. Blue OLEDs remain the most sought-after devices in terms of combination of stability and high performance compared to other monochromatic EL colors (see Bhansali et al., 2009).

Figure 6:
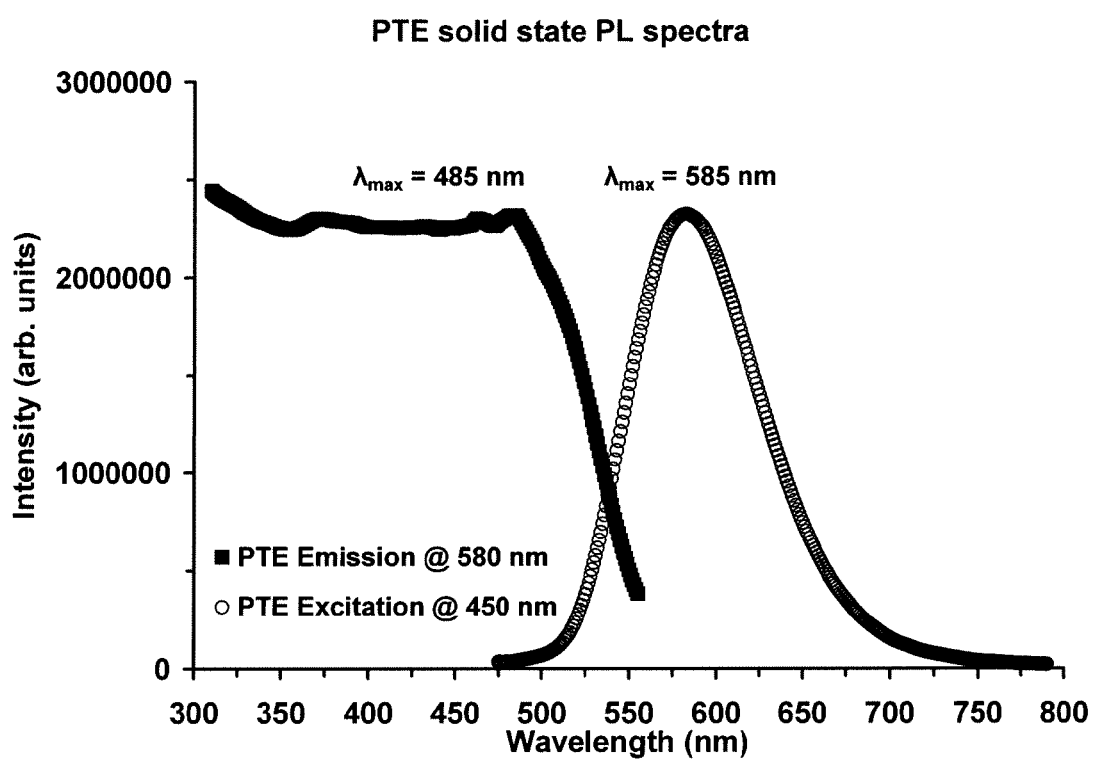
FIG. 6 shows the PL spectra of PTE.

PTE has yellow-orange emission with a peak maximum at 585 nm. It has a high quantum yield of 74% and short phosphorescent lifetime of 0.376 µs in the powder form. It also has high chemical stability and thermal stability over 300° C. Photoluminescence ("PL") spectra are shown in FIG. 6.

Figure 7:
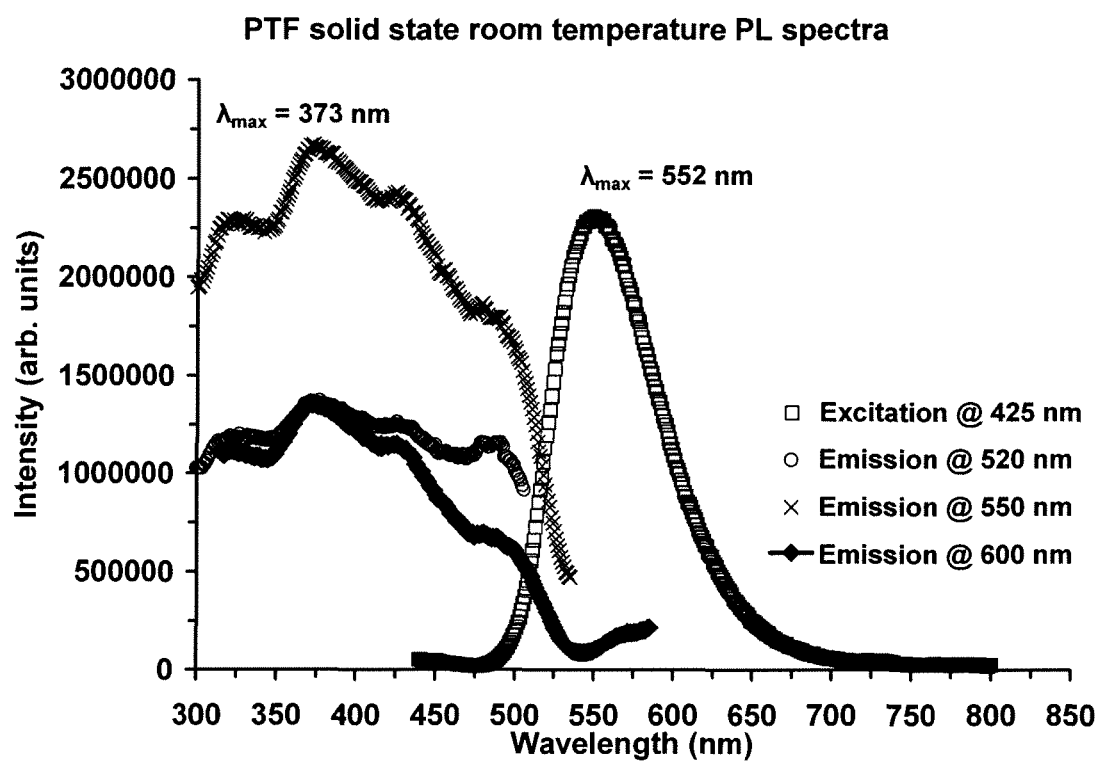
FIG. 7 shows the PL spectra of PTF.

PTF has yellow emission with a peak maximum at 572 nm. It has a high quantum yield of 81% and short phosphorescent lifetime of 0.774 µs in the powder form. It also has high chemical stability and thermal stability over 300° C. PL spectra are shown in FIG. 7.

Figure 8:
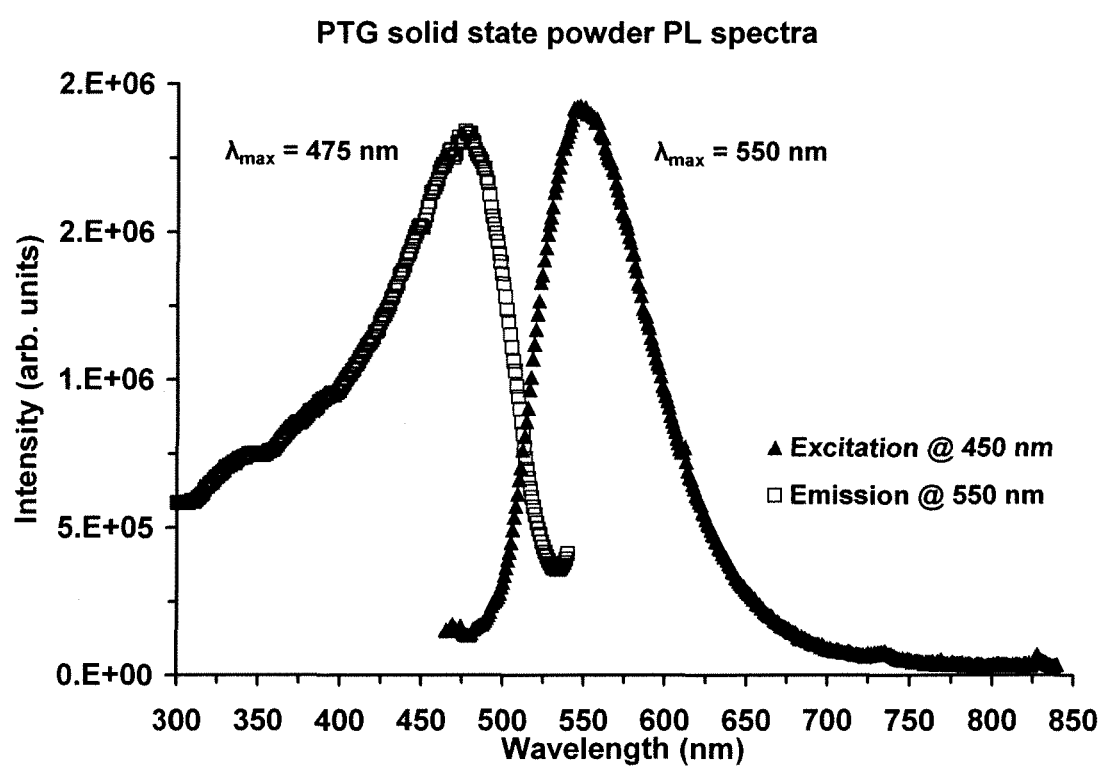
FIG. 8 shows the PL spectra of PTG.

PTG has green-yellow emission with a peak maximum at 552 nm. It has a moderate quantum yield of 18% and short phosphorescent lifetime of 0.523 µs in the powder form. It also has high chemical stability and thermal stability over 350° C. PL spectra are shown in FIG. 8.

Figure 9:
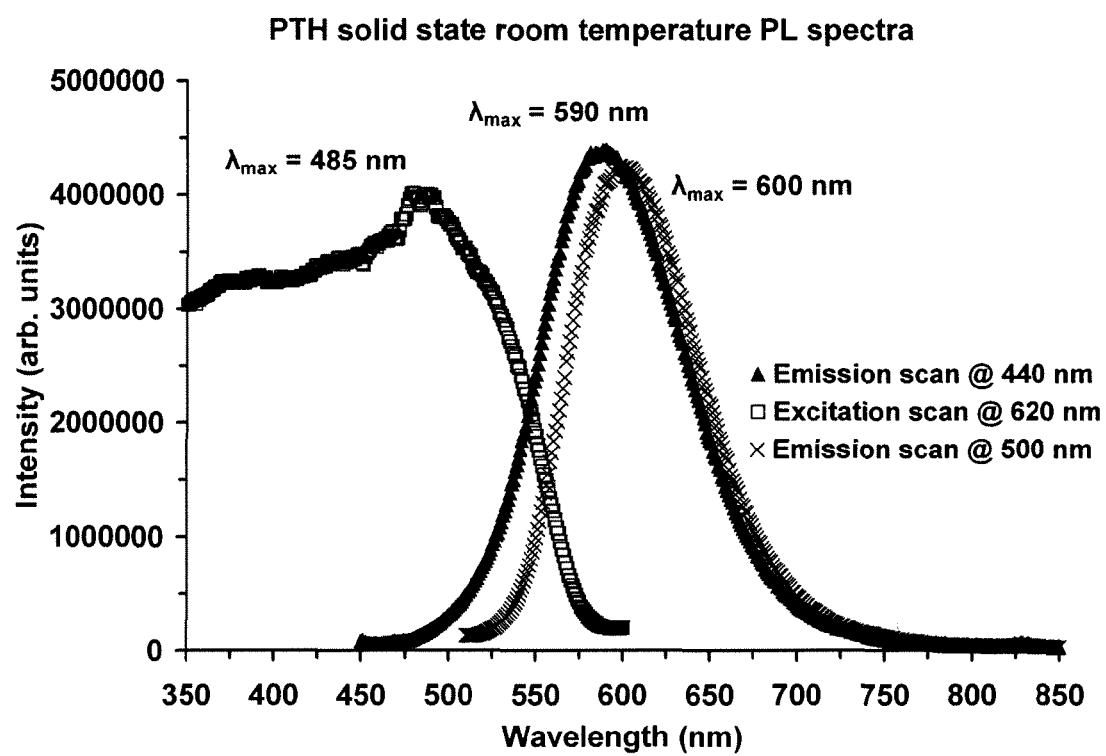
FIG. 9 shows the PL spectra of PTH.

PTH has orange emission with a peak maximum at 590 nm. It has a high quantum yield of 51% and short phosphorescent lifetime of 0.382 µs in the powder form. It also has high chemical stability and thermal stability over 300° C. PL spectra are shown in FIG. 9.

Figure 10:
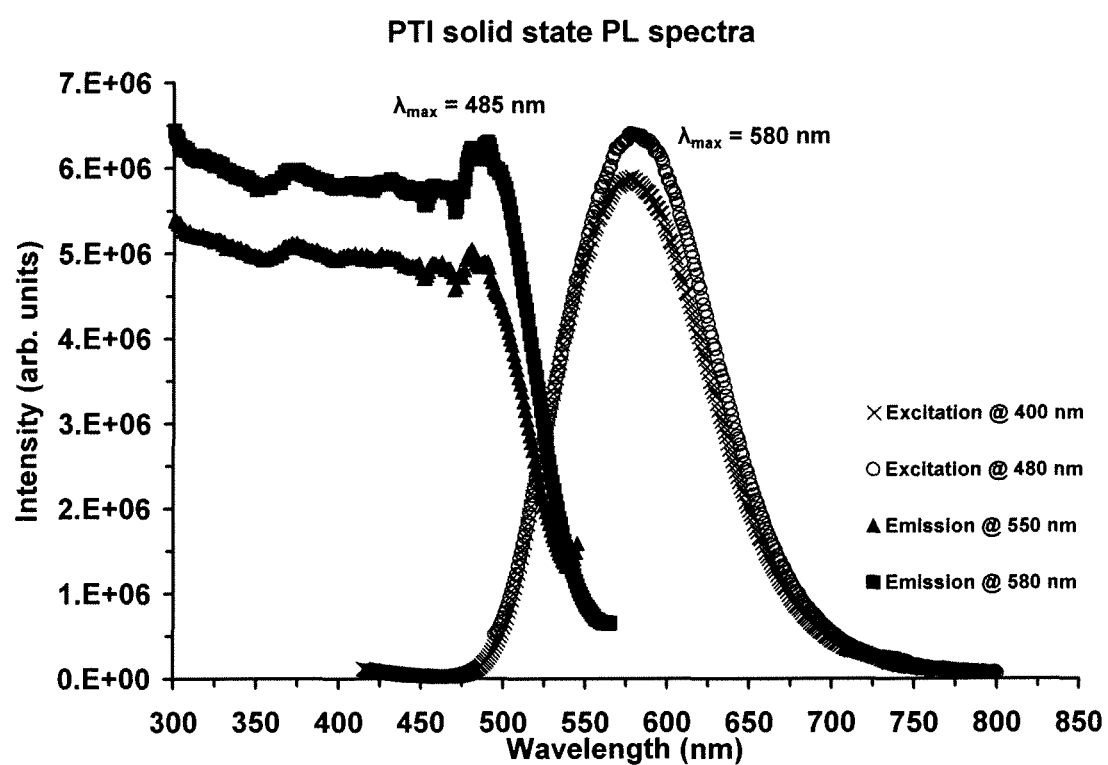
FIG. 10 shows the PL spectra of PTI.

PTI has yellow-orange emission with a peak maximum at 570 nm. It has a high quantum yield of 45% and short phosphorescent lifetime of 0.324 µs in the powder form. It also has high chemical stability and thermal stability over 300° C. PL spectra are shown in FIG. 10.

Figure 11:
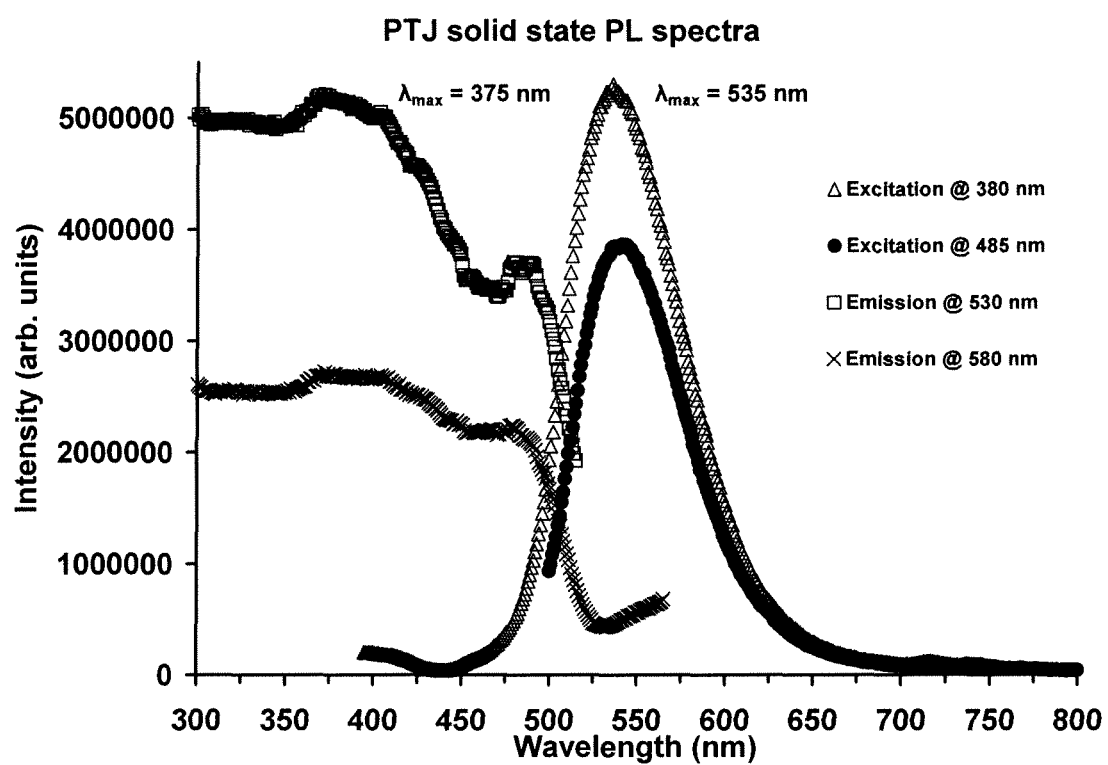
FIG. 11 shows the PL spectra of PTJ.

PTJ has green emission with a peak maximum at 535 nm. It has a high quantum yield of 56% and short phosphorescent lifetime of 0.340 µs in the powder form. It also has high chemical stability and thermal stability over 300° C. PL spectra are shown in FIG. 11.

Figure 12:
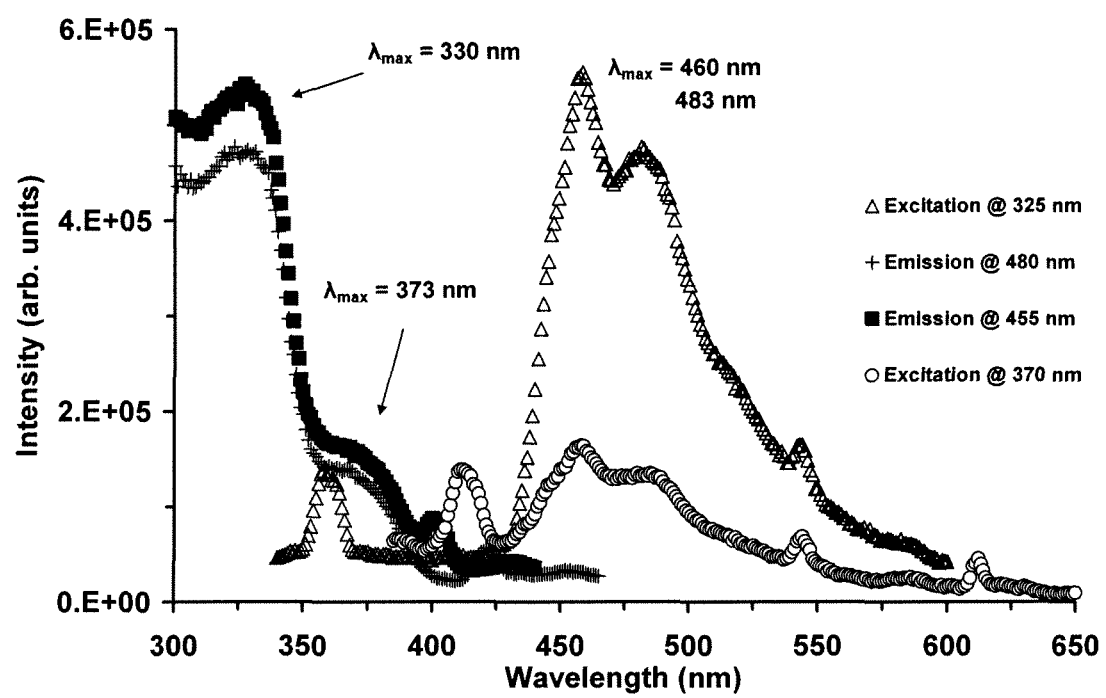
FIG. 12 shows the PL spectra of PTE at $1 \times 10^{-4}$ M concentration in dioxane solution.
Figure 13:
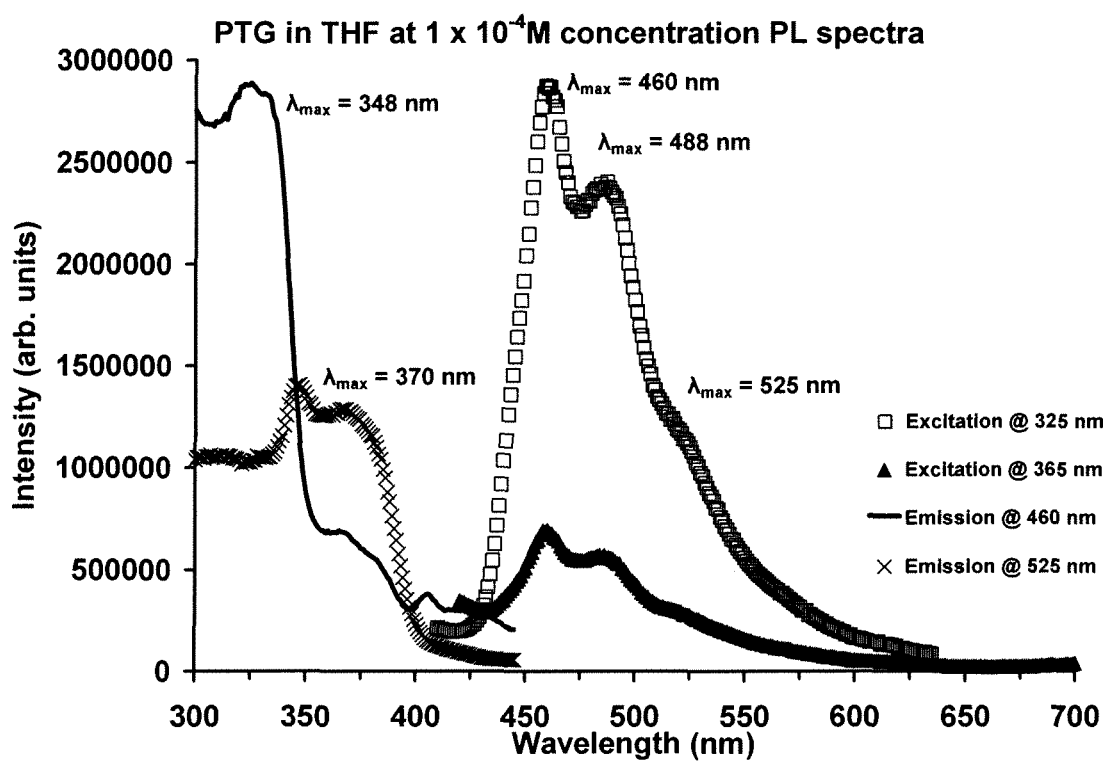
FIG. 13 shows the PL spectra of PTG at $1 \times 10^{-4}$ M concentration in THF solution.

The data in FIGS. 12 and 13 shows the PL spectra for dilute solutions of PTE and PTG respectively. At low concentrations (1×10$^{-4}$M), these species exhibit structured emission from the monomer rather than an aggregate due to the intermolecular distances being much larger than in the solid state. These data show that these materials, when doped at sufficient concentrations, could act as efficient blue phosphors, which is currently the most highly sought after color in OLEDs.

EXAMPLE 3

Electroluminescence Data

OLED Devices were fabricated using PTD. A neat device using PTD was fabricated according to the FIG. 17. The device consisted of 5 layers: an ITO glass anode, a 60 nm TAPC hole carrying layer, a 90 nm thick PTD layer acting concomitantly as the electron transport layer and emissive layer, and a lithium fluoride cathode. The device is doping-free which implies that PTD is functioning as the electron transporting material as well as the emissive material. The device has a peak maximum at 580 nm, indicating the emission is from an aggregate state rather than a monomer.

Figure 14:
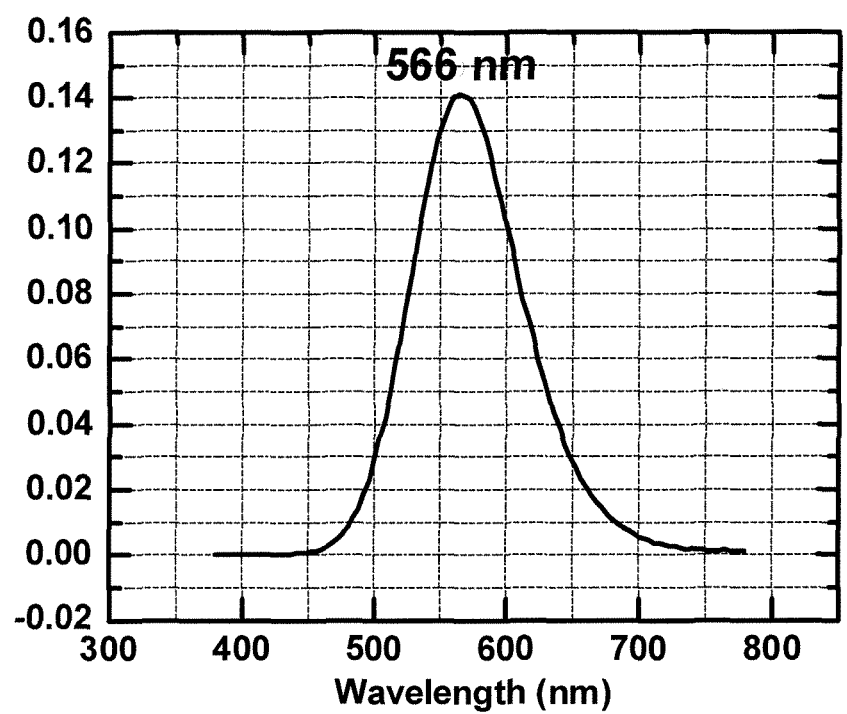
FIG. 14 shows the electroluminescence spectra of PTD in a neat device.
Figure 15:
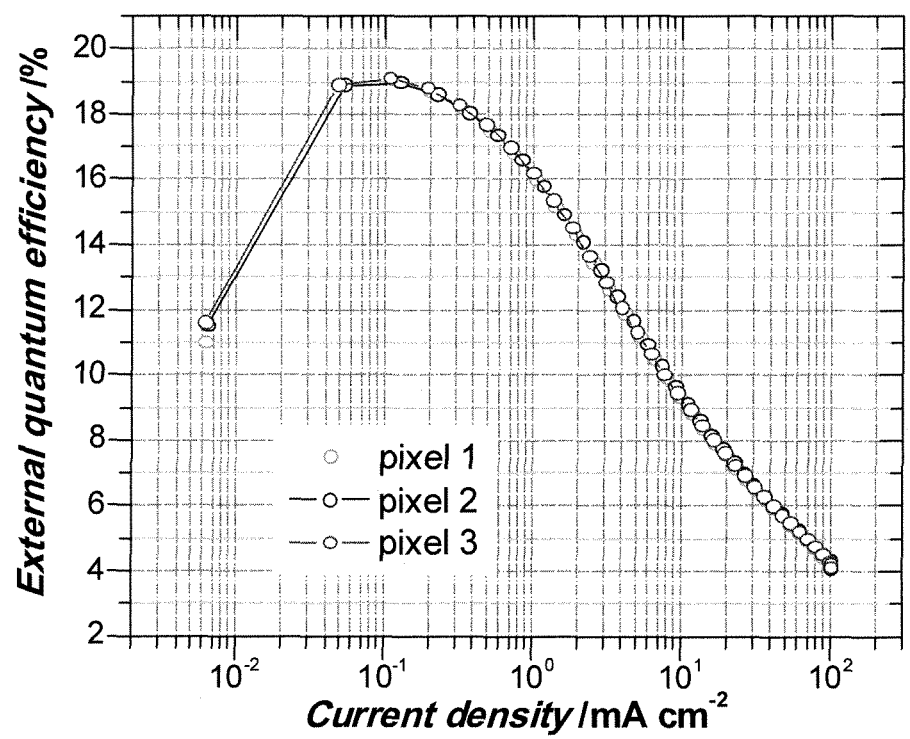
FIG. 15 shows the external quantum efficiency of PTD in a neat device.
Figure 16:
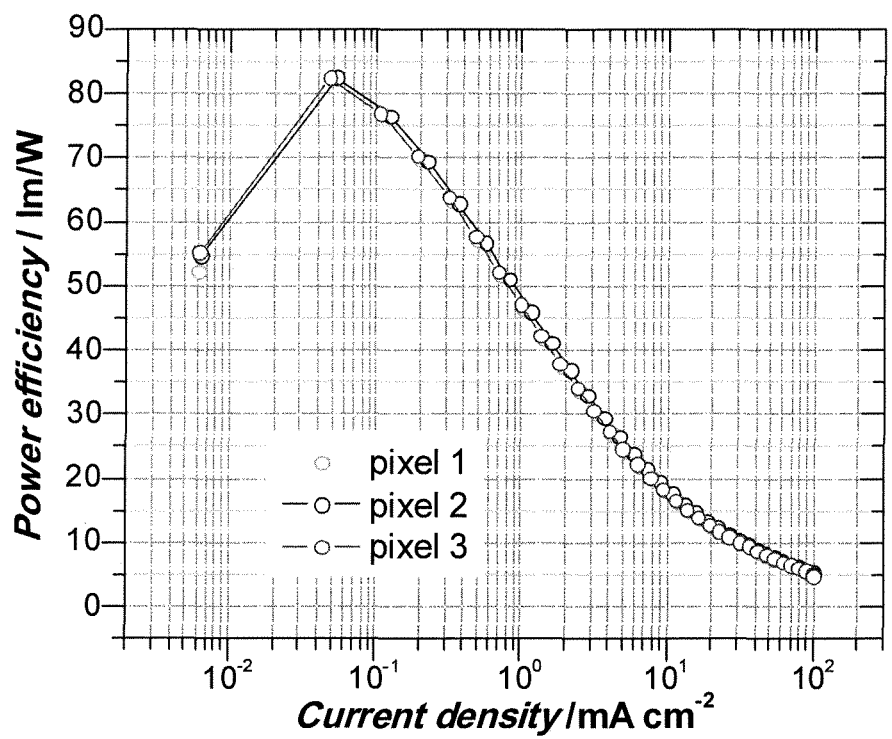
FIG. 16 shows the power quantum efficiency of PTD in a neat device.
Figure 17:
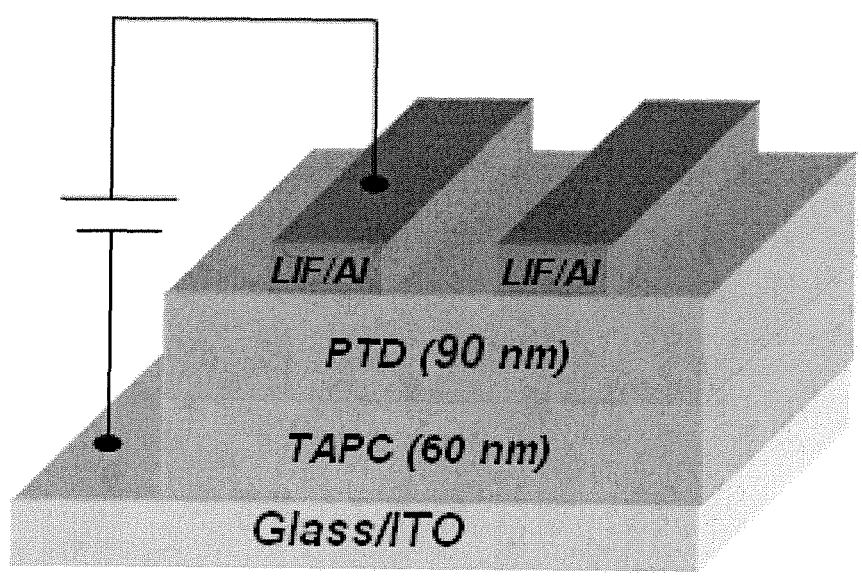
FIG. 17 shows a schematic of the neat PTD device architecture.
Figure 18:
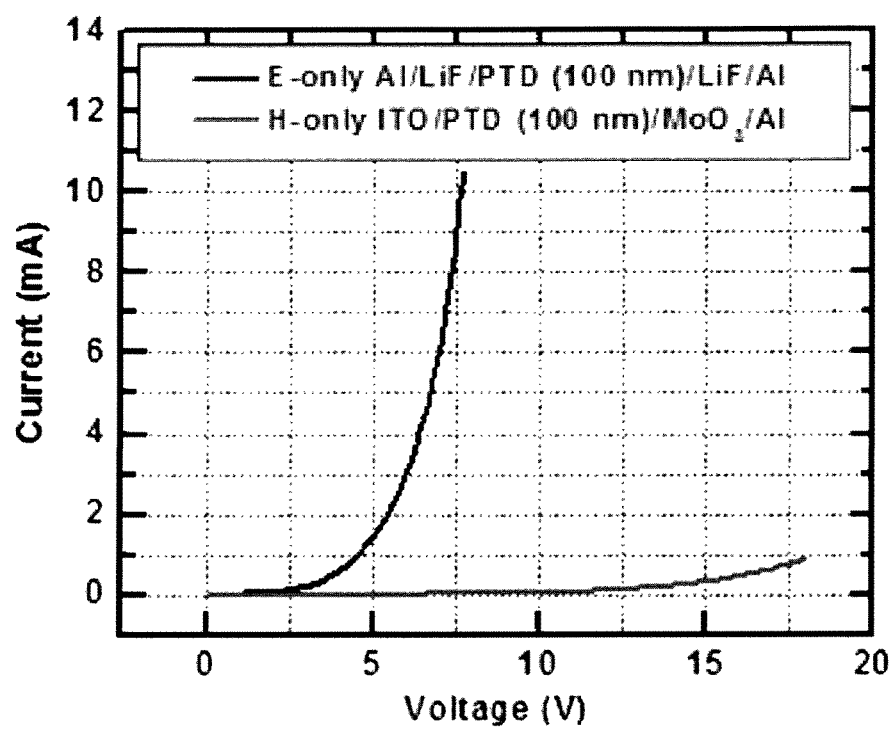
FIG. 18 shows the I-V curve of single carrier electron and hole only devices.

FIGS. 14-16 show representative electroluminescence (EL) data, external quantum efficiency (EQE), and power efficiency (PE) data for these OLEDs using PTD functioning as the electron transfer layer (ETL) and the emissive layer (EML) in a bi-layer device structure as seen in FIG. 17. The EL spectrum in FIG. 14 shows a similar spectral profile to that seen in FIG. 5 above indicating that the mechanism for emission (e.g. the aggregate as opposed to the monomer emission) is the same for both. The best monochromatic device had a maximum power efficiency of 82 lm/W (FIG. 15), and an EQE of ~19% (FIG. 16) with a low threshold voltage of 2.9V. These values are among the highest reported for a monochromatic bi-layer doping-free device architecture and show that these materials can compete with the current state-of-the-art doped OLED devices. FIG. 18 shows current-voltage curves for single carrier electron-only and hole-only devices. The electron-only devices (Al/LiF/PTD (100 nm)/LiF/Al), wherein only electrons can be transported due to the low workfunction of the Al/LiF anode and LiF/Al cathode, and the hole-only devices (ITO/PTD (100 nm)/ $MoO_3$/Al), wherein only holes can be transported due to the high workfunction of the ITO anode and $MoO_3$/Al cathode, were based on neat PTD. Inserting a thin $MoO_3$ layer (3 nm) before Al in the cathode in the hole-only device prevents electron injection into PTD. The electron-only device shows significant current at increasing voltages with a low threshold voltage of 2.2V, but negligible current in the hole-only device. This demonstrates that this material is capable of efficiently transporting electrons yet cannot transport holes, indicating strictly n-type semiconducting behavior over p-type or ambipolar behavior. This phenomenon allows this material, and by inference (via chemical intuition based on the structural composition and spectral properties) others in this family of materials, to be used as an electron-transporting material and/or emissive layer leading to simplified devices.

EXAMPLE 4

X-Ray Structural Data

Figure 19:
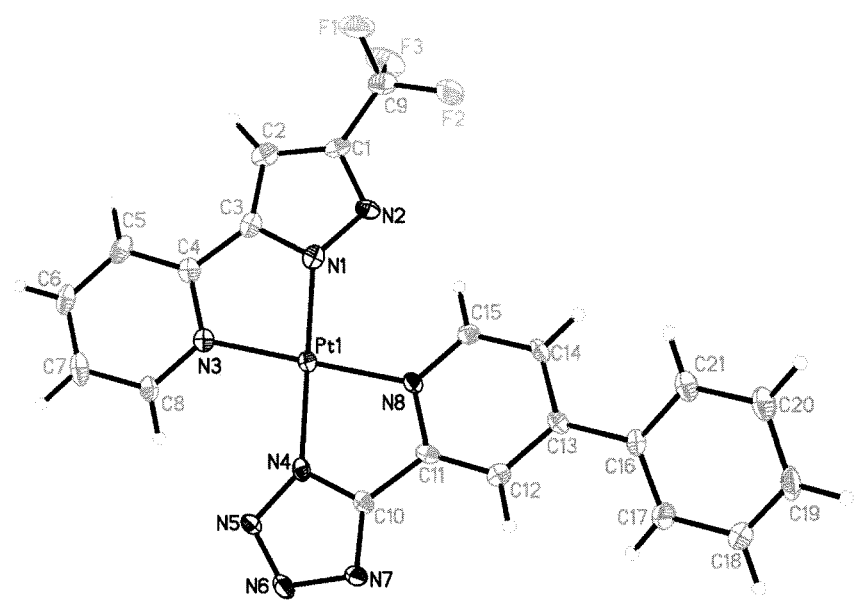
FIG. 19 shows one unit of the PTE crystal structure.
Figure 20:
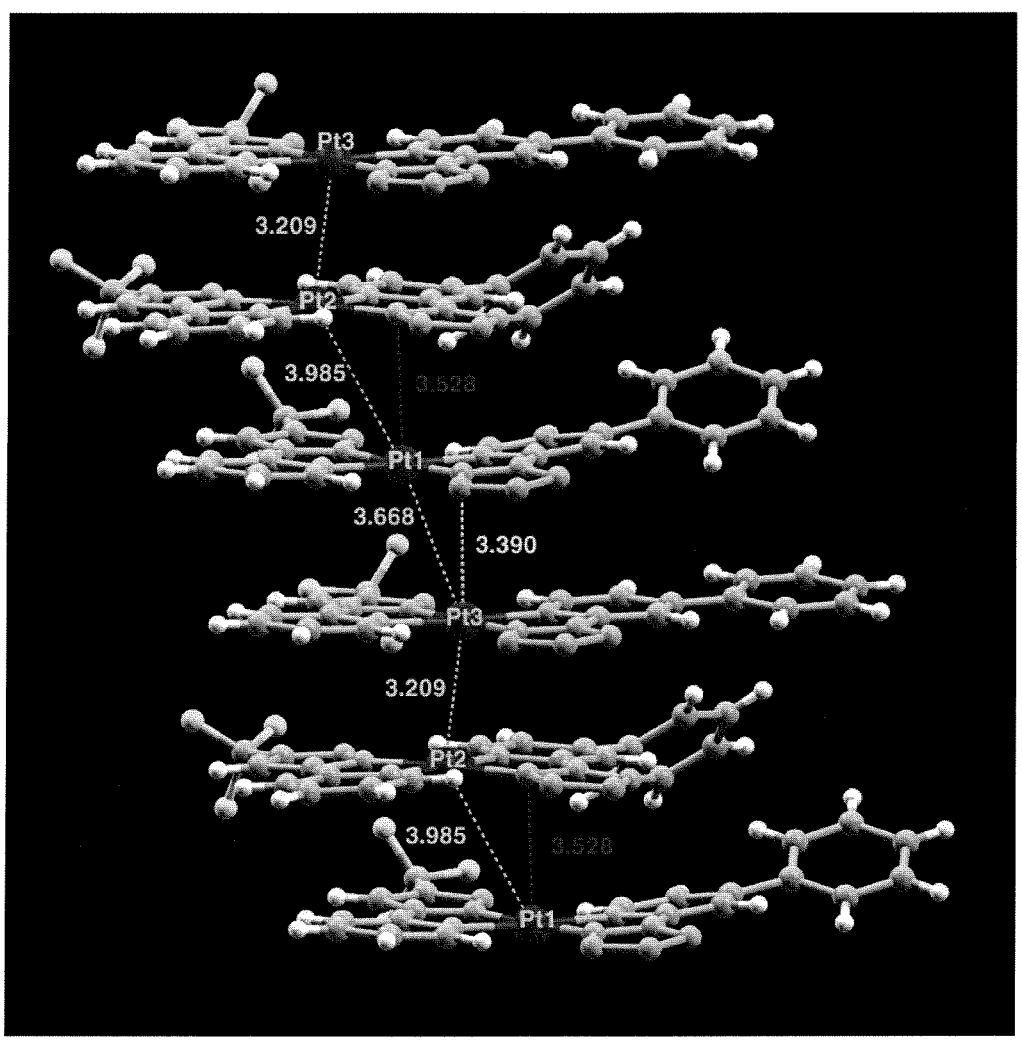
FIG. 20 shows the packing motif of PTE with 6 discreet units.

Crystals of PTE and PTG show both materials exhibiting similar vertical chain packing motifs. PTE, shown in FIG. 19, exhibits a unique stacking pattern where the topmost molecule (Pt3 center) is essentially completely planar while the middle (Pt2 center) and bottom (Pt1 center) molecules have slight distortions disrupting their planarity and vertical alignment (FIG. 20). The middle molecule is aligned vertically such that its Pt2 center is directly below the Pt3 center with a distance of 3.209 Å. The Pt2- and Pt3-centered molecules are offset by roughly 30°, as defined by the N1B-Pt3-Pt2-N1A torsion angle. Unlike the Pt3 molecule, the Pt2 molecule is not completely planar: The phenyl group in the 4-position of the pyridine ring on the pyridyltetrazolate moiety is rotated out of plane by 32°. This is presumably due to steric hindrance as the Pt2 molecule is sandwiched between the Pt3 and Pt1 molecules. There are also neighboring dioxane solvent molecules near the phenyl ring, which increases crowding, and thus help push it out of plane. Finally, the Pt1 molecule does not have vertical alignment of its platinum atom with the Pt2 and Pt3 molecules above it. Although the Pt3 and Pt2 molecules have linear vertical alignment of their platinum atoms, Pt1 is translated in the xy plane with a relatively long distance between Pt1 and Pt2 (3.985 Å). This distance is beyond the van der Waals separation, rendering relatively insignificant Pt—Pt interaction. However, the offset position of the Pt1 molecule in relation to the Pt2 and Pt3 molecules does allow for interactions between the azolate rings that sandwich it. FIG. 2.14 shows that t tetrazolate ring above is 3.528 Å and the distance bet he distance between Pt1 and the ween Pt1 and the pyrazolate ring below is 3.414 Å. In addition, a short distance of 3.390 Å was found between the tetrazolate moiety in the Pt1 molecule and the platinum atom, Pt3 below.

Figure 21:
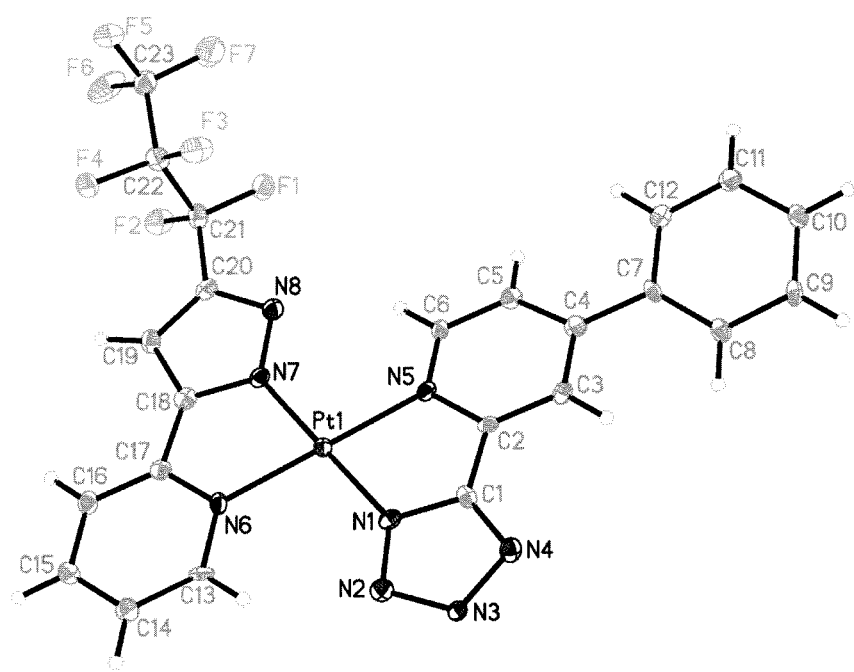
FIG. 21 shows one unit of the PTG crystal structure.
Figure 22:
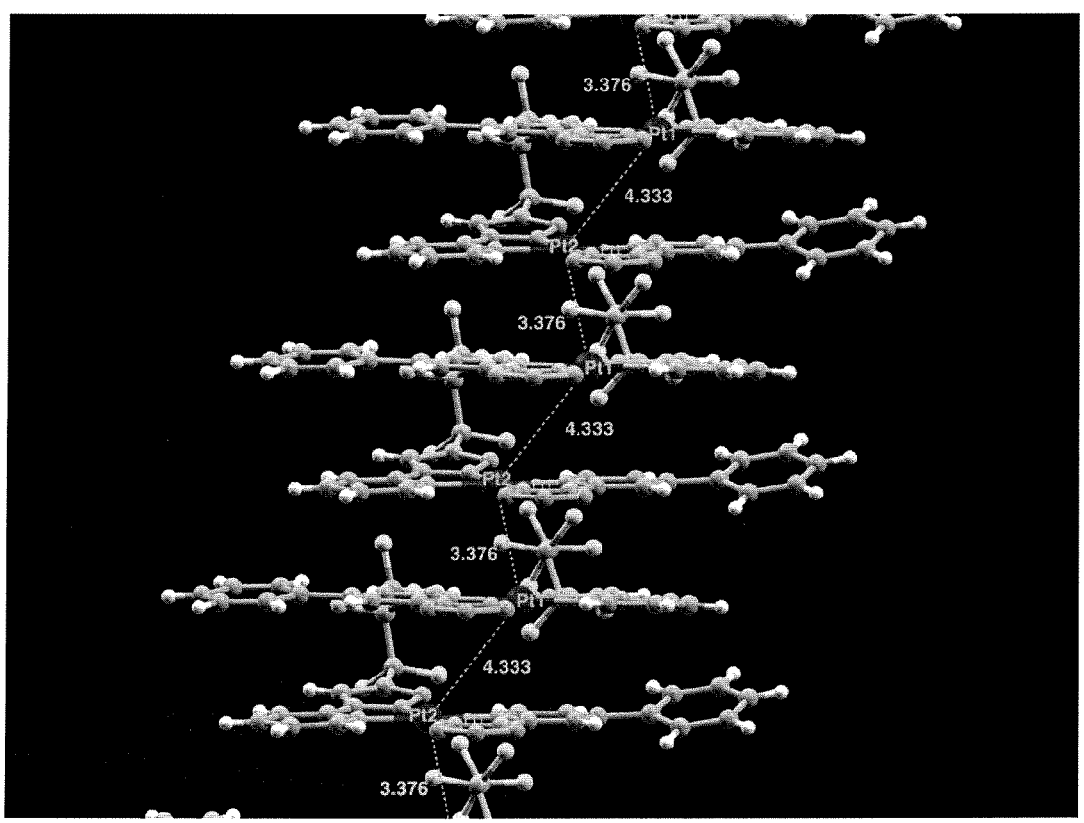
FIG. 22 shows the packing motif of PTG.

Crystals of PTG were grown using slow evaporation of THF to yield large yellow needles that exhibited mild yellow luminescence at room temperature and intense green at 77K. FIG. 21 shows a single molecular unit. The structure does not include any solvent molecules. The molecules stack vertically in infinite columns similar to PTE in sets of dimers. Each dimer consists of a short Pt—Pt distance of 3.376 Å while the neighboring dimers above and below are separated at a distance of 4.333 Å (shown in FIG. 22). The large distance of 4.333 Å is greater than the Van der Waals radius of two platinum atoms thus minimizing any significant Pt—Pt interaction. The perfluoropropyl moieties in each vertical column orient such that they are on the same side and aligned between neighboring stacks, creating a double-layered fluorous surface between stacks. Within the dimers, the electronegative tetrazolate moiety of the Pt1 molecule and the more electropositive pyrazolate moiety of the Pt2 molecule orient to maximize overlap, giving strong electrostatic interactions.

REFERENCES CITED

The following publications are hereby incorporated by reference.

OTHER PUBLICATIONS

Bentiss, F.; Lagrenee, M.; Vezin, H.; Bouanis, M.; Mernari, B.; *Journal of Heterocyclic Chemistry*, 2002, 39, 93.
Bhansali, U.; Polikarpov, E.; Swensen, J. S.; Chen, W.-H.; Jia, H.; Gaspar, D. J.; Gnade, B. E.; Padmaperuma, A. B.; Omary, M. A., *Appl. Phys. Lett.* 2009, 95, 233304.
D'Andrade, B. W.; Forrest, S. R. "White Organic Light-Emitting Devices for Solid-State Lighting", *Adv. Mater.* 2004, 16, 1585.
D'Andrade, B. W.; Adamovich, V.; Thompson, M. E.; Forrest, S. "White Light Emission Using Triplet Excimers in Electrophosphorescent Organic Light-Emitting Devices" *Adv. Matt.* 2002, 14, 1032.
Misra, A.; Kumar, P.; Kamalasanan, M. N.; Chandra, S. "White organic LEDs and their recent advancements", *Semicond. Sci. Technol.* 2006, 21, R35-R47.
Myznikov, L. V.; Roh, J.; Artamonova, T. V.; Hrabalek, A.; Koldobskii, G. I. *Russ. J. Org. Chem.* 2007, 43, 765-767.
Newman, C. R.; Frisbie, C. D.; da Silva Filho, D. A.; Bredas, J.-L.; Ewbank, P. C.; Mann, K. R. "Introduction to Organic Thin Film Transistors and Design of n-Channel Organic Semiconductors" *Chem. Mater.* 2004, 16, 4436.
Sloop, J. C.; Bumgardner, C. L.; Washington, G.; Loehle, W. D.; Sankar, S. S.; Lewis, A. B. *J. Fluor. Chem.* 2006, 127, 780-786.
Thiel, W. R.; Eppinger, *J. Chem. Eur. J.* 1997, 3, 696-705.
Wang, Q.; Oswald, I. W. H.; Perez, M. R.; Huiping, J; Gnade, B. E.; Omary, M. A. *Adv. Funct. Mater.* 2013, 23, 5420-5428.
Omary, M. A. U.S. Pat. No. 8,580,397, issued Nov. 12, 2013.

What is claimed is:
1. A plurality of bidentate heteroleptic square planar complexes of (pyridyl)azolates having the general structure:

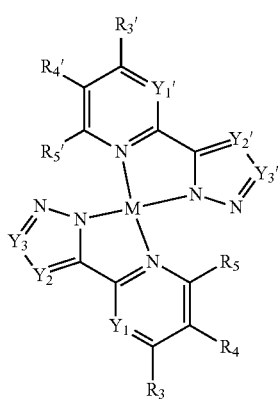

wherein:
the plurality of bidentate heteroleptic square planar complexes of (pyridyl)azolates comprise a first bidentate ligand having substituents and a second bidentate ligand having substituents and both bidentate ligands are complexed to M;

M is Pt, Pd, or Ni;

$Y_1$ is C—$R_2$ or N;

$Y_1'$ is C—$R_2'$ or N;

$Y_2$ and $Y_2'$ are independently C—H or N;

$Y_3$ is C—$R_1$ or N, wherein $Y_3$ is C—$R_1$ only when $R_2$ and $R_2'$ are not H;

$Y_3'$ is N;

$R_1$ and $R_1'$ are independently H, $CF_3$, $C_3F_7$, $C_6F_5$, $C_6H_5$, $CH_3$, or $C_5H_4N$;

$R_2$ and $R_2'$ are independently H, $CH_3$, $CF_3$, $C_3F_7$, $C_2H_5$, $C_3H_7$, $C_6H_5$, $C_6F_5$, or $C_5H_4N$;

$R_3$ and $R_3'$ are independently H, $CH_3$, $CF_3$, $C_3F_7$, $C_2H_5$, $C_3H_7$, $C_6H_5$, $C_6F_5$, $C_{10}H_7$, $C_{13}H_9$, $C_{14}H_9$, $C_5H_4N$, or $C_{12}H_8N$;

$R_4$ and $R_4'$ are independently H, $CH_3$, $CF_3$, $C_3F_7$, $C_2H_5$, $C_3H_7$, $C_6H_5$, $C_6F_5$, $C_{10}H_7$, $C_{13}H_9$, $C_{14}H_9$, $C_{12}H_8N$, or $C_5H_4N$;

$R_5$ and $R_5'$ are independently H or F;

wherein the first bidentate ligand is not identical to the second bidentate ligand bonded to the same metal such that at least one among $R_1$, $R_2$, $R_3$, $R_4$, $R_5$, $Y_1$, $Y_2$, and $Y_3$ species on the first ligand is different from $R_1'$, $R_2'$, $R_3'$, $R_4'$, $R_5'$, $Y_1'$, $Y_2'$, and $Y_3'$ on the second ligand and wherein optionally, one or more among $R_1$, $R_2$, $R_3$, $R_4$, $R_5$, $R_1'$, $R_2'$, $R_3'$, $R_4'$, $R_5'$, $Y_1$, $Y_2$, $Y_3$, $Y_1'$, $Y_2'$, and $Y_3'$ is identical on two ligands where at least one of $R_1$, $R_2$, $R_3$, $R_4$, $R_5$, $R_1'$, $R_2'$, $R_3'$, $R_4'$, $R_5'$, $Y_1$, $Y_2$, $Y_3$, $Y_1'$, $Y_2'$, or $Y_3'$ is different in the other ligand complexed to M; and wherein the plurality of bidentate heteroleptic square planar complexes of (pyridyl)azolates aggregate together upon packing in a solid or crystalline state.

2. A plurality of bidentate heteroleptic square planar complexes of (pyridyl)azolates of claim 1, wherein the bidentate heteroleptic square planar complexes of (pyridyl)azolates are [(5-(2-pyridyl)-1,2,3,4-tetrazolato)(3-trifluoromethyl-5-(2-pyridyl)-1,2-pyrazolato)]Platinum(II), [(5-(5-phenyl-2-pyridyl)-1,2,3,4-tetrazolato)(3-trifluoromethyl-5-(2-pyridyl)-1,2-pyrazolato)]Platinum(II), [(5-(2-pyridyl)-1,2,3,4-tetrazolato)(3-heptafluoropropyl-5-(2-pyridyl)-1,2-pyrazolato)]Platinum(II), [(5-(5-phenyl-2-pyridyl)-1,2,3,4-tetrazolato)(3-heptafluoropropyl-5-(2-pyridyl)-1,2-pyrazolato)]Platinum(II), [(5-(6-methyl-2-pyridyl)-1,2,3,4-tetrazolato)(3-trifluoromethyl-5-(2-pyridyl)-1,2-pyrazolato)]Platinum(II), [(5-(4-fluoro-2-pyridyl)-1,2,3,4-tetrazolato)(3-trifluoromethyl-5-(2-pyridyl)-1,2-pyrazolato)]Platinum(II), or [(5-(4-fluoro-2-pyridyl)-1,2,3,4-tetrazolato)(3-heptafluoropropyl-5-(2-pyridyl)-1,2-pyrazolato)]Platinum(II).

3. The plurality of bidentate heteroleptic square planar complexes of (pyridyl)azolates of claim 1, wherein M is Pd or Ni.

4. The plurality of bidentate heteroleptic square planar complexes of (pyridyl)azolates of claim 1, wherein at least one of $R_1$, $R_2$, $R_3$, $R_4$, $R_5$, $R_1'$, $R_2'$, $R_3'$, $R_4'$, or $R_5'$ is H.

5. The plurality of bidentate heteroleptic square planar complexes of (pyridyl)azolates of claim 1, wherein the bidentate heteroleptic square planar complexes of (pyridyl)azolates are [(5-(2-pyridyl)-1,2,3,4-tetrazolato)(3-trifluoromethyl-5-(2-pyridyl)-1,2-pyrazolato)]Platinum(II) and wherein the bidentate heteroleptic square planar complexes of (pyridyl)azolates have semi-conducting behavior.

6. The plurality of bidentate heteroleptic square planar complexes of (pyridyl)azolates of claim 1, wherein the bidentate heteroleptic square planar complexes of (pyridyl)azolates are [(5-(5-phenyl-2-pyridyl)-1,2,3,4-tetrazolato)(3-trifluoromethyl-5-(2-pyridyl)-1,2-pyrazolato)]Platinum(II), [(5-(2-pyridyl)-1,2,3,4-tetrazolato)(3-heptafluoropropyl-5-(2-pyridyl)-1,2-pyrazolato)]Platinum(II), [(5-(5-phenyl-2-pyridyl)-1,2,3,4-tetrazolato)(3-heptafluoropropyl-5-(2-pyridyl)-1,2-pyrazolato)]Platinum(II), [(5-(6-methyl-2-pyridyl)-1,2,3,4-tetrazolato)(3-trifluoromethyl-5-(2-pyridyl)-1,2-pyrazolato)]Platinum(II), [(5-(4-fluoro-2-pyridyl)-1,2,3,4-tetrazolato)(3-trifluoromethyl-5-(2-pyridyl)-1,2-pyrazolato)]Platinum(II), or [(5-(4-fluoro-2-pyridyl)-1,2,3,4-tetrazolato)(3-heptafluoropropyl-5-(2-pyridyl)-1,2-pyrazolato)]Platinum(II) and wherein the bidentate heteroleptic square planar complexes of (pyridyl)azolates have high thermal stability at temperatures less than 300° C.

7. An organic light emitting diode comprising the plurality of bidentate heteroleptic square planar complexes of (pyridyl)azolates of claim 1.

8. The organic light emitting diode of claim 7, wherein the plurality of bidentate heteroleptic square planar complexes of (pyridyl)azolates are contained in a layer that functions as both an electron transport layer and an emissive layer.

9. The organic light emitting diode of claim 8, wherein the organic light emitting diode further comprises an ITO anode, a 4,4'-cyclohexylidenebis[N,N-bis(4-methylphenyl)benzeneamine hole carrying layer, and a lithium fluoride cathode.

10. The organic light emitting diode of claim 7, wherein the organic light emitting diode is white, near-white, or monochromatic.

11. The organic light emitting diode of claim 7, wherein the organic light emitting diode is free of doping.

12. The organic light emitting diode of claim 7, wherein the plurality of bidentate heteroleptic square planar complexes of (pyridyl)azolates are [(5-(2-pyridyl)-1,2,3,4-tetrazolato)(3-trifluoromethyl-5-(2-pyridyl)-1,2-pyrazolato)]Platinum(II).

13. The organic light emitting diode of claim 7, wherein the plurality of bidentate heteroleptic square planar complexes of (pyridyl)azolates are [(5-(2-pyridyl)-1,2,3,4-tetrazolato)(3-trifluoromethyl-5-(2-pyridyl)-1,2-pyrazolato)]Platinum(II) and wherein the organic light emitting diode has a maximum power efficiency of about 82 lm/W, an external quantum efficiency of about 19%, and a low threshold voltage of about 2.9V.

14. The organic light emitting diode of claim 7, wherein the plurality of bidentate heteroleptic square planar complexes of (pyridyl)azolates are a blue emitting neat form and the organic light emitting diode generates blue phosphorescence.

15. Organic thin film transistors comprising the plurality of bidentate heteroleptic square planar complexes of (pyridyl)azolates of claim 1.

16. The organic thin film transistors of claim 15, wherein the organic thin film transistors are n-type organic thin film transistors.

17. Complementary metal-oxide semiconductor device architectures comprising the organic thin film transistors of claim 15.

18. Semiconducting solids comprising the plurality of bidentate heteroleptic square planar complexes of (pyridyl) azolates of claim 1, wherein the semiconducting solids are films, single crystals, or pressed pellets.

19. A plurality of bidentate heteroleptic square planar complexes of (pyridyl)azolates, wherein the bidentate heteroleptic square planar complexes of (pyridyl)azolates are [(5-(2-pyridyl)-1,2,3,4-tetrazolato)(3-trifluoromethyl-5-(2-pyridyl) -1,2-pyrazolato)]Platinum(II), [(5-(5-phenyl-2-pyridyl)-1,2,3,4-tetrazolato)(3-trifluoromethyl -5-(2-pyridyl)-1,2-pyrazolato)]Platinum(II), [(5-(2-pyridyl)-1,2,3,4-tetrazolato) (3-heptafluoropropyl-5-(2-pyridyl)-1,2-pyrazolato)]Platinum(II), [(5-(5-phenyl-2-pyridyl) -1,2,3,4-tetrazolato)(3-heptafluoropropyl-5-(2-pyridyl)-1,2-pyrazolato)]Platinum(II), [(5-(6-methyl-2-pyridyl)-1,2,3,4-tetrazolato)(3-trifluoromethyl-5-(2-pyridyl)-1,2-pyrazolato)]Platinum(II), [(5-(4-fluoro-2-pyridyl)-1,2,3,4-tetrazolato)(3-trifluoromethyl -5-(2-pyridyl)-1,2-pyrazolato)]Platinum(II), or [(5-(4-fluoro-2-pyridyl)-1,2,3,4-tetrazolato)(3-heptafluoropropyl-5-(2-pyridyl)-1,2-pyrazolato)]Platinum(II).

20. An organic light emitting diode comprising the plurality of bidentate heteroleptic square planar complexes of (pyridyl)azolates of claim 19.

21. Semiconducting solids comprising the plurality of bidentate heteroleptic square planar complexes of (pyridyl) azolates of claim 19, wherein the semiconducting solids are films, single crystals, or pressed pellets.

22. Organic thin film transistors comprising the plurality of bidentate heteroleptic square planar complexes of (pyridyl)azolates of claim 19.

23. Complementary metal-oxide semiconductor device architectures comprising the organic thin film transistors of claim 22.

* * * * *